US008265756B1

(12) United States Patent
Snell et al.

(10) Patent No.: US 8,265,756 B1
(45) Date of Patent: Sep. 11, 2012

(54) SYSTEM AND METHOD FOR ADJUSTING AUTOMATIC SENSITIVITY CONTROL PARAMETERS BASED ON INTRACARDIAC ELECTROGRAM SIGNALS

(75) Inventors: Jeffery D. Snell, Chatsworth, CA (US); Rupinder Bharmi, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 707 days.

(21) Appl. No.: 11/608,154

(22) Filed: Dec. 7, 2006

(51) Int. Cl.
*A61N 1/06* (2006.01)
(52) U.S. Cl. .............................. 607/27; 607/28; 600/509
(58) Field of Classification Search .................. 600/509; 607/4, 5, 9, 27–29
See application file for complete search history.

(56) References Cited

U.S. PATENT DOCUMENTS

| 5,269,300 | A | * | 12/1993 | Kelly et al. | 607/4 |
| 5,339,820 | A | | 8/1994 | Henry et al. | |
| 5,685,315 | A | | 11/1997 | McClure et al. | |
| 5,906,633 | A | | 5/1999 | Mouchawar et al. | |
| 6,321,115 | B1 | | 11/2001 | Mouchawar et al. | |
| 6,377,851 | B1 | * | 4/2002 | Shieh et al. | 607/9 |
| 6,493,584 | B1 | | 12/2002 | Lu | |
| 6,553,259 | B2 | | 4/2003 | Mouchawar et al. | |
| 6,625,490 | B1 | * | 9/2003 | McClure et al. | 607/9 |
| 6,650,931 | B1 | | 11/2003 | McClure et al. | |
| 6,711,438 | B1 | | 3/2004 | McClure et al. | |
| 6,862,476 | B2 | * | 3/2005 | Mouchawar et al. | 607/27 |
| 6,947,794 | B1 | | 9/2005 | Levine | |
| 7,155,282 | B1 | | 12/2006 | Min et al. | |
| 7,392,087 | B2 | * | 6/2008 | Zhang et al. | 607/28 |
| 2003/0097157 | A1 | * | 5/2003 | Wohlgemuth et al. | 607/27 |
| 2004/0106957 | A1 | | 6/2004 | Palreddy et al. | |
| 2006/0085038 | A1 | | 4/2006 | Linder et al. | |

FOREIGN PATENT DOCUMENTS

| EP | 0581010 A2 | 2/1994 |
| EP | 0581010 A3 | 2/1994 |

OTHER PUBLICATIONS

Castro, Antonio et al., "Evaluation of Autosensing as an Automatic Means of Maintaining a 2:1 Sensing Safety Margin in an Implanted Pacemaker," PACE 1996; 19(Pt. II):1708-1713.

Schulte, Britta et al., "Inappropriate Arrhythmia Detection in Implantable Defibrillator Therapy due to Oversensing of Diaphragmatic Myopotentials," Journal of Interventional Cardiac Electrophysiology 5; 487-493, 2001.

Weretka, Slawomir et al., "Ventricular Oversensing: A Study of 101 Patients Implanted with Dual Chamber Defibrillators and Two Different Lead Systems," PACE 2003; 26(Pt. I):65-70.

(Continued)

*Primary Examiner* — Niketa Patel
*Assistant Examiner* — Joseph Stoklosa

(57) ABSTRACT

Systems and methods are provided for use by an implantable medical device capable of automatically adjusting the sensitivity with which electrical cardiac signals are sensed within a patient, i.e. a device equipped with Automatic Sensitivity Control (ASC.) In a first example, ASC parameters are automatically adjusted by the device itself based on parameters derived from both R-waves and T-waves and further based on a detected noise floor. In a second example, a profile representative of the shape of cardiac signals is generated by the device. ASC parameters are then adjusted based on the profile. In various embodiments, histograms are used to determine sizes and shapes of the R-waves and T-waves via statistical prevalence techniques. The histograms are also employed to derive the aforementioned profile.

8 Claims, 15 Drawing Sheets

OTHER PUBLICATIONS

Israel, Carsten W., "Mode-switching algorithms: programming and usefulness," Herz. Feb. 2001;26(1):2-17.

Scher, David L., "Troubleshooting pacemakers and implantable cardioverter-defibrillators," Curr Opin Cardiol. Jan. 2004;19(1):36-46.

NonFinal Office Action, mailed Apr. 5, 2010—Related U.S. Appl. No. 11/608,168.

Final Office Action, mailed Sep. 14, 2010—Related U.S. Appl. No. 11/608,168.

* cited by examiner

SYSTEM AND METHOD FOR ADJUSTING AUTOMATIC SENSITIVITY CONTROL PARAMETERS BASED ON INTRACARDIAC ELECTROGRAM SIGNALS

CROSS-REFERENCE TO RELATED APPLICATIONS

This application is related to copending U.S. patent application Ser. No. 11/608,168, filed concurrently herewith, titled "System and Method for Adjusting Automatic Sensitivity Control Parameters Based on Intracardiac Electrogram Signals".

FIELD OF THE INVENTION

The invention generally relates to implantable cardiac stimulation devices, such as pacemakers or implantable cardioverter/defibrillators ("ICDs") and, in particular, to techniques for use with devices equipped to perform automatic sensitivity control (ASC).

BACKGROUND OF THE INVENTION

A pacemaker is an implantable cardiac stimulation device for implant within a patient that analyzes an intracardiac electrogram (IEGM) to detect various arrhythmias, such as an abnormally slow heart rate (bradycardia) or an abnormally fast heart rate (tachycardia), and then selectively delivers electrical pacing pulses to the heart in an effort to remedy the arrhythmias. An implantable cardioverter-defibrillator (ICD) additionally or alternatively detects atrial fibrillation (AF) or ventricular fibrillation (VF) and delivers electrical shocks to terminate fibrillation. Such devices are typically configured to be used in conjunction with an external programmer that enables a physician to program the operation of an implanted device to, for example, control the specific parameters by which the pacemaker detects arrhythmias and responds thereto. In particular, the physician may program a set of parameters that the device uses to automatically control the sensitivity with which the device senses electrical signals within the heart. The sensitivity determines the amplitude of signals to which the device's sense amplifiers will respond, typically specified in millivolts (mV). The higher the mV value, the lower the sensitivity. For example, if the sensitivity is set to 6 mV, a signal must be at least 6 mV before the signal will be recognized. If the sensitivity is only set to 2 mV, the signal need only be 2 mV before it is recognized. Hence, the lower the mV value, the more sensitive the device.

State-of-the-art pacemakers and ICDs are equipped with ASC, which is a procedure by which the device automatically adjusts atrial and ventricular sensitivity values during each individual cardiac cycle to keep the values at optimum levels. ASC and related techniques are discussed in U.S. Pat. No. 6,862,476 to Mouchawar, et al., entitled "Implantable Cardiac Stimulation Device Having Automatic Sensitivity Control and Method." Current implementations of ASC are specified by several programmable parameters including: Starting Sensitivity, Decay Delay, Decay Rate, Maximum Sensitivity and Refractory Period, which depend upon whether ASC is applied to paced and/or sensed events and which further depend on whether ASC is applied to atrial and/or ventricular events. These parameters will now be described primarily with reference to a ventricular ASC example.

With ventricular ASC, the ventricular sensitivity is initially set to the Starting Sensitivity value immediately following delivery of a ventricular pacing pulse (i.e. a V-pulse) or detection of an R-wave (i.e. a ventricular depolarization event, also referred to as QRS-complex). The ventricular Starting Sensitivity is specified as a percentage of the average amplitude of prior R-waves and is typically set to a relatively high percentage value (e.g. 50%-90%) so as to provide a relatively high mV value (thus making the ventricular sense amplifier relatively insensitive to further signals at this time). The ventricular sensitivity remains at the Starting Sensitivity level for the duration of the ventricular Decay Delay interval. Separate Decay Delay values are used following sensed ventricular events (i.e. R-waves) and paced ventricular events (i.e. V-pulses.) Once the appropriate ventricular Decay Delay interval has elapsed, the device automatically and gradually decreases the ventricular sensitivity mV value in accordance with a ventricular Decay Rate (thus making the ventricular sense amplifier increasingly more sensitive to further signals.) The ventricular sensitivity continues to increase (i.e. the mV value continues to decrease) until the ventricular sensitivity reaches a ventricular Maximum Sensitivity (i.e. a minimum mV value) or until another R-wave is detected or another V-pulse is delivered. The ventricular Maximum Sensitivity thereby represents the maximum permissible sensitivity of the ventricular sense amplifier (or the minimum permissible sensitivity mV value).

Once another R-wave is detected (or another V-pulse is delivered), the ventricular sensitivity mV value is then bumped up to the Starting Sensitivity value (thus making the ventricular sense amplifier again less sensitive) and the process repeats. Additionally, ventricular refractory (VREF) intervals are activated after initial detection an R-wave. During VREF, any signals sensed by the ventricular sense amplifier are ignored, at least for the purposes of triggering or inhibiting pacing pulses. The signals can nevertheless be examined and recorded for diagnostic purposes. Separate VREF values are used following R-waves and V-pulses. A similar ASC procedure may be performed for the atrial sense amplifier to automatically adjust an atrial sensitivity following detection of an atrial depolarization event (also referred to as a P-wave) or delivery of a atrial pacing pulse (i.e. an A-pulse.)

Hence, during ASC, the device automatically adjusts the atrial and ventricular sensitivity values during each cardiac cycle (i.e. each heartbeat.) This is performed to enhance the specificity with which atrial and ventricular events are detected. In particular, on the ventricular channel, the ventricular sensitivity mV value is initially kept at a relatively high level following each R-wave/V-pulse to prevent the corresponding T-wave (i.e. ventricular repolarization) from being erroneously detected and misinterpreted as another R-wave (which is referred to as "oversensing"). The ventricular sensitivity mV value is ultimately lowered to help ensure that the next R-wave of the next cardiac cycle is properly detected. For the atrial channel, the atrial sensitivity mV value is initially kept at a relatively high level following each P-wave/A-pulse to prevent the far-field R-waves (i.e. R-waves generated in the ventricles but sensed in the atria) from being erroneously detected and misinterpreted as P-waves. The atrial sensitivity mV value is ultimately lowered to help ensure that the P-wave of the next cardiac cycle is properly detected. By helping to prevent erroneous detection of T-waves, far-field R-waves, etc., ASC thereby helps ensure that atrial and ventricular rates are reliably detected so that pacing or defibrillation therapy, if need, can be reliably and appropriately delivered. (Note that, strictly speaking, P-waves, R-waves and T-waves are features of the surface electrocardiogram (EKG). For convenience and generality, the terms P-wave, R-wave and T-wave are used herein to refer to the corresponding internally-detected signal components, i.e. the corresponding components of the IEGM. The amplitudes and widths of these features and the intervals therebetween are also referred to herein as morphological features of the cardiac signal.)

FIG. 1 illustrates a set of exemplary ventricular ASC parameters 2 in connection with stylized ventricular cardiac signals 4 associated with intrinsic ventricular depolarizations. Atrial ASC parameters are generally similar, but are defined relative to P-waves (which are not shown in FIG. 1). Exemplary ventricular ASC values are as follows. Starting Sensitivity may be programmed to 50% of present R-wave amplitudes. The ventricular post-sensed and post-paced Decay Delay values may both be set to 60 milliseconds (ms). The ventricular Decay Rate may be set to 3 mV/second. The ventricular Maximum Sensitivity may be set to 0.3 mV. VREF(sensed) may be set to 125 ms). VREF(paced) may be set to 250 ms. Atrial values typically differ from their corresponding ventricular values. For example, atrial post-sensed and post-paced atrial Decay Delay values may both be set to 0 ms. The atrial Decay Rate may be set to 1.5 mV/second. The post-sensed atrial refractory period (AREF) may be set to 93 ms). AREF(paced) may be set to 190 ms. With current devices, the ventricular and atrial ASC parameters are programmed by a physician or other clinician using an external programmer device following device implant. Thereafter, the ASC parameters are not changed until a follow-up programming session. That is, the various ASC parameters are fixed parameters that are not automatically adjustable by the device itself. Moreover, although ASC controls sensitivity in response to changes in R-wave amplitude (by setting the Starting Sensitivity mV value based on a percentage of R-wave amplitude), ASC does not take into account changes in T-wave amplitude.

Hence, although ASC is a very effective technique for automatically adjusting sensitivity throughout each cardiac cycle, there is room for further improvement. In particular, cardiac signal amplitudes, including T-wave amplitudes as well as R-wave and P-wave amplitudes, may fluctuate depending on lead maturation and fibrosis, lead micro-dislodgement, patient activity, drug intake and a variety of other factors, such that ASC parameters specified by the physician may no longer be appropriate. In this regard, most physicians perform a sensing threshold test during a follow-up session with the patient and then set the ASC parameters accordingly. Unfortunately, the selected parameters may not be appropriate during subsequent episodes of cardiac signal instability. As such, if the resulting sensitivity set by the ASC procedure is too low, some cardiac events will not be detected. If the sensitivity set by ASC is too high, erroneous sensing of noise may occur or undesired cardiac signals may be incorrectly classified. Sensing problems can potentially result in abnormal/inappropriate device function, inappropriate therapy, incorrect diagnostic data collection, inappropriate arrhythmia detection and inappropriate mode switching.

Inappropriate sensing may occur in a patient in many forms. For example, over-sensing on the ventricular channel can cause T-waves to be erroneously counted as R-waves. Over-sensing on the atrial channel can cause far-field R-waves to be mistaken as P-waves. Noise over-sensing on either channel (possibly resulting from diaphragmatic myopotentials, skeletal myopotentials, etc.) can cause noise to be mistaken as P-waves or R-waves. Under-sensing may arise due to a decrease in P-wave or R-wave amplitudes, where the amplitude variation may result from respiration effects, exercise, or the presence of an arrhythmia. In particular, atrial arrhythmia typically causes a reduction in P-wave amplitude to as little as ⅕th of the true P-wave amplitude. Other factors such as drugs or electrolyte imbalances can cause inappropriate sensing. In addition, patients with cardio-myopathies are more prone to sensing malfunctions. Several other factors may also affect the device's sensitivity over a period of time, such as fibrotic tissue growth, lead micro dislodgment, lead fracture and changes due to defibrillation shock.

Thus, the programmable ASC parameters may need to be frequently adjusted by the physician to compensate for noise or other factors. However, patients are typically not monitored by the physician more frequently than once every six months; and often less frequently. Hence, the implanted device may operate incorrectly (or at least sub-optimally) for six months or more before the ACS parameters are adjusted by the physician.

Some techniques have been proposed that appear to allow a Maximum Sensitivity-type parameter to be automatically adjusted by the device based on a detected noise floor. See, e.g., U.S. Patent Application 2006/0085038 of Linder et al., entitled "Method And Apparatus For Adjusting Cardiac Event Detection Threshold Based On Dynamic Noise Estimation"; U.S. Patent Application 2003/0097157, of Wohlgemuth et al., entitled "Implantable Medical Device With Autosensitivity Algorithm For Controlling Sensing Of Cardiac Signals"; and U.S. Patent Application 2004/0106957 of Palreddy et al., entitled "Method and System for Noise Measurement in an Implantable Cardiac Device." Adjusting the Maximum Sensitivity value based on a noise floor helps address some sensing problems that arise due to variations in signal channel noise. However, other sensing problems, particularly those arising due to changes in the morphology of the cardiac signal, are not corrected merely by taking noise into account. Moreover, the techniques described within the aforementioned patent applications are not necessarily applicable to ASC, which, as explained, is a particular type of sensitivity adjustment technique that employs a particular set of programmable parameters. Also, it does not appear that the predecessor techniques specifically detect the sizes and shapes of T-waves for the purposes of adjusting ASC parameters so as to optimize R-wave detection while avoiding T-wave oversensing.

Accordingly, it would be highly desirable to provide techniques for remedying problems that arise in devices equipped to perform ASC and it is to that end that the invention is primarily directed.

SUMMARY OF THE INVENTION

Systems and methods are provided for use by an implantable medical device capable of automatically adjusting a sensitivity with which electrical cardiac signals are sensed within a patient wherein the sensitivity adjusted during individual cardiac cycles in accordance with a predetermined adjustment procedure specified by a plurality of programmable sensitivity adjustment parameters.

In a first general embodiment, electrical cardiac signals are sensed and parameters representative of depolarization and repolarization events are detected within the electrical cardiac signals. The programmable sensitivity adjustment parameters are then set or adjusted by the device based both on the parameters representative of depolarization events and the parameters representative of repolarization events. Hence, unlike those predecessor devices where the programmable sensitivity adjustment parameters can only be set or adjusted by a clinician, with the exemplary technique the programmable sensitivity adjustment parameters are instead set or adjusted by the device itself, allowing it to automatically respond to changes in both R-waves and T-waves.

In one example, wherein the device is equipped to perform ASC, the programmable parameters that are automatically adjusted by the device are ASC parameters, specifically: a Starting Sensitivity parameter specifying a Starting Sensitivity for use following detection of a sensed event; a Decay Delay parameter specifying a duration of time following the sensed event before sensitivity is automatically decreased; a Maximum Sensitivity parameter that specifies a maximum permissible sensitivity; a Refractory Interval specifying a duration of time following a sensed event during which any further events are not sensed; and a Decay Rate specifying a rate by which the sensitivity is changed following completion of the Decay Delay. The parameters representative of depolarization and repolarization events that are used to adjust the ASC parameters include: a depolarization amplitude (R-wave amplitude); a repolarization amplitude (T-wave amplitude); a depolarization width (R-wave width); a repolarization width (T-wave width); and an interval between depolarization and repolarization events (RT interval), as detected using either near-field signals, far-field signals, or both.

In one illustrative example, an amount of electrical noise with the cardiac signals is also detected. Then, Maximum Sensitivity is either periodically or continuously adjusted based on the amount of electrical noise so as to remain above a noise floor. Starting Sensitivity is set based on a programmable percentage of the detected R-wave amplitude so long as the resulting Starting Sensitivity value does not exceed the Maximum Sensitivity value (i.e. so that the Starting Sensitivity mV value is not set below the Maximum Sensitivity mV value). Decay Delay is adjusted based on the duration of the RT interval. In one specific example, the Decay Delay is set equal to the RT interval plus a safety margin. In that example, the Decay Rate is then set to a maximum permissible Decay Rate value so as to cause the sensitivity to immediately switch to the Maximum Sensitivity value. That is, in that particular example, the sensitivity is not gradually changed. Rather, the sensitivity jumps from the Starting Sensitivity to the Maximum Sensitivity immediately upon completion of the Decay Delay. In other examples, the Decay Delay and the Decay Rate are set based on the RT interval, the T-wave amplitude and the T-wave width so as to permit the sensitivity to gradually change following the Decay Delay while still avoiding T-wave over-sensing. The Refractory Interval is preferably set based on R-wave width. In other examples, a floating Refractory Interval is specified so as to encompass the expected location of the T-wave.

Preferably, the various adjustments are made using not just the latest IEGM signals detected within the patient but also using statistical characteristics of R-waves and T-waves derived for the patient. In this manner, the device does not react improperly to changes in detected parameters that are merely temporary or short-term. Rather, the device responds to changes that are more likely to be of long-term significance. Preferably, a separate set of ASC parameters are specified for the atrial and ventricular channels. Likewise, a separate set of ASC parameters are preferably specified depending upon whether depolarization events (i.e. P-waves and R-waves) are paced or sensed. Histograms may be employed to track the morphological features of the cardiac signals, including amplitudes and widths of P-waves, R-waves and T-waves and intervals therebetween. Expected values of the morphological parameters are then derived from the histograms to aid in adjusting the ASC parameters. The expected value may be derived using statistical prevalence techniques.

Additionally, or alternatively, a variety of more specific ASC parameter adjustment procedures may be performed based on the relative sizes of the morphological features of the cardiac signals. In a first specific example, where the T-wave is small and the R-wave width is nominal but the R-wave amplitude is large, then nominal (i.e. preprogrammed) ASC parameters may be used. For example, the Starting Sensitivity is set to 60% of the R-wave amplitude, the Decay Delay is set to 30 ms, the Decay Rate is set to 3 mV/second, and the Ventricular Refractory period is set 100 ms or other a preprogrammed duration. Nominal ASC parameters may be used since the R-wave has a much greater amplitude than the T-wave, and so T-wave over-sensing is not a significant risk. In a second specific example, where the T-wave and R-wave amplitudes are both large (and the R-wave width is nominal), then a combination of the modified ASC parameters are employed to avoid over-sensing of the T-wave: the Starting Sensitivity is set higher than its nominal value; the Decay Delay is set to be longer than nominal; and a longer VREF is used. A slower Decay Delay may also be employed. In this case, since the T-wave also has a large amplitude, nominal ASC parameters are not used. Rather, the parameters are modified to cause the sensitivity mV value to being decreasing later and more slowly so that it remains above the mV value of the T-wave.

In a third specific example, where the R-wave amplitude and width are both nominal and the T-wave amplitude is minimal, then Starting Sensitivity is preferably set to 50% of the R-wave amplitude, Decay Delay is preferably set to zero, and the Ventricular Refractory period is preferably set 100 ms or other a preprogrammed duration. A Decay Delay of zero is preferred since the T-wave amplitude is minimal and hence T-wave over-sensing is not a problem. By immediately increasing the sensitivity to the Maximum Sensitivity value, prompt and reliable detection of the next R-wave is achieved, even in cases of ventricular tachycardia. In a fourth specific example, where the R-wave width is wider than nominal and the T-wave amplitude is minimal, then Starting Sensitivity is again preferably set to 50% of the R-wave amplitude, Decay Delay is again preferably set to zero, but the Ventricular Refractory period is preferably set to the R-wave width plus a preprogrammed safety margin of 25 ms. The Ventricular Refractory is set in this manner to account for the wider R-wave so as to prevent possible double R-wave over-sensing. In a fifth specific example, wherein the R-wave amplitude is larger than nominal and the T-wave amplitude is minimal, then Starting Sensitivity is again preferably set to 50% of the R-wave amplitude and Decay Delay is again preferably set to zero. As with the first specific example, a Decay Delay of zero is preferred since the T-wave amplitude is minimal and hence T-wave over-sensing is not a problem.

In a sixth specific example, where the R-wave amplitude is larger than nominal and the T-wave amplitude is nominal, Starting Sensitivity is again preferably set to 50% of the R-wave amplitude, Decay Delay is preferably set equal to the RT interval plus a safety margin, and Decay Rate is preferably set to a nominal rate (such as 3 mV/second). In this example, with a big R-wave and a T-wave of normal size, the Decay Delay is set based on the RT interval to ensure that the sensitivity does not begin decreasing so soon that T-wave over-sensing occurs. In a fifth specific example, where R-wave amplitude is nominal and T-wave amplitude is also nominal, then Starting Sensitivity is preferably set to 90% of the R-wave amplitude, Decay Delay is preferably set equal to the RT interval plus the safety margin, and Decay Rate is preferably set to a predetermined nominal rate, e.g. 3 mV/second. In this example, with a normal-sized R-wave and a normal-sized T-wave, the Starting Sensitivity mV value is set higher than usual to again ensure that T-wave over-sensing does not occur. In a seventh specific example, where the R-wave amplitude is minimal and the T-wave amplitude is large, then Starting Sensitivity is preferably set to 75% of the R-wave amplitude, Decay Delay is again preferably set to equal to the RT interval plus a safety margin, and a floating Ventricular Refractory period is employed that encompasses the repolarization event. The floating refractory period is used to prevent T-wave over-sensing, while still permitting R-wave sensing despite minimal R-wave amplitudes. In still other examples, the Decay Rate is set based on the RT interval and the T-wave width to avoid T-wave over-sensing.

In a second general embodiment of the invention, electrical cardiac signals are sensed and a profile representative of the shape of the cardiac signals is determined. The programmable sensitivity adjustment parameters are then adjusted based on the profile. By exploiting a profile representing the shape of the cardiac signal, the sensitivity adjustment parameters may thereby be set so as to avoid over-sensing while still substantially ensuring that features of interest (i.e. P-waves or R-waves) are detected. In one example, histograms are used to derive a profile representative of the shape of cardiac signals. In that example, the ASC parameters are then set based on the profile to substantially eliminate over-sensing or under-sensing problems.

Thus, improved techniques are provided for use with automatic sensitivity adjustment procedures, particularly ASC, that avoids problems with the predecessor techniques discussed above. System and method implementations are set forth.

BRIEF DESCRIPTION OF THE DRAWINGS

Further features and advantages of the invention may be more readily understood by reference to the following description taken in conjunction with the accompanying drawings, in which.

DETAILED DESCRIPTION OF THE PREFERRED EMBODIMENTS

The following description includes the best mode presently contemplated for practicing the invention. The description is not to be taken in a limiting sense but is made merely for the purpose of describing the general principles of the invention. The scope of the invention should be ascertained with reference to the issued claims. In the descriptions that follow, like numerals or reference designators are used to refer to like parts or elements throughout.

Overview of Implantable Medical System

Figure 1:
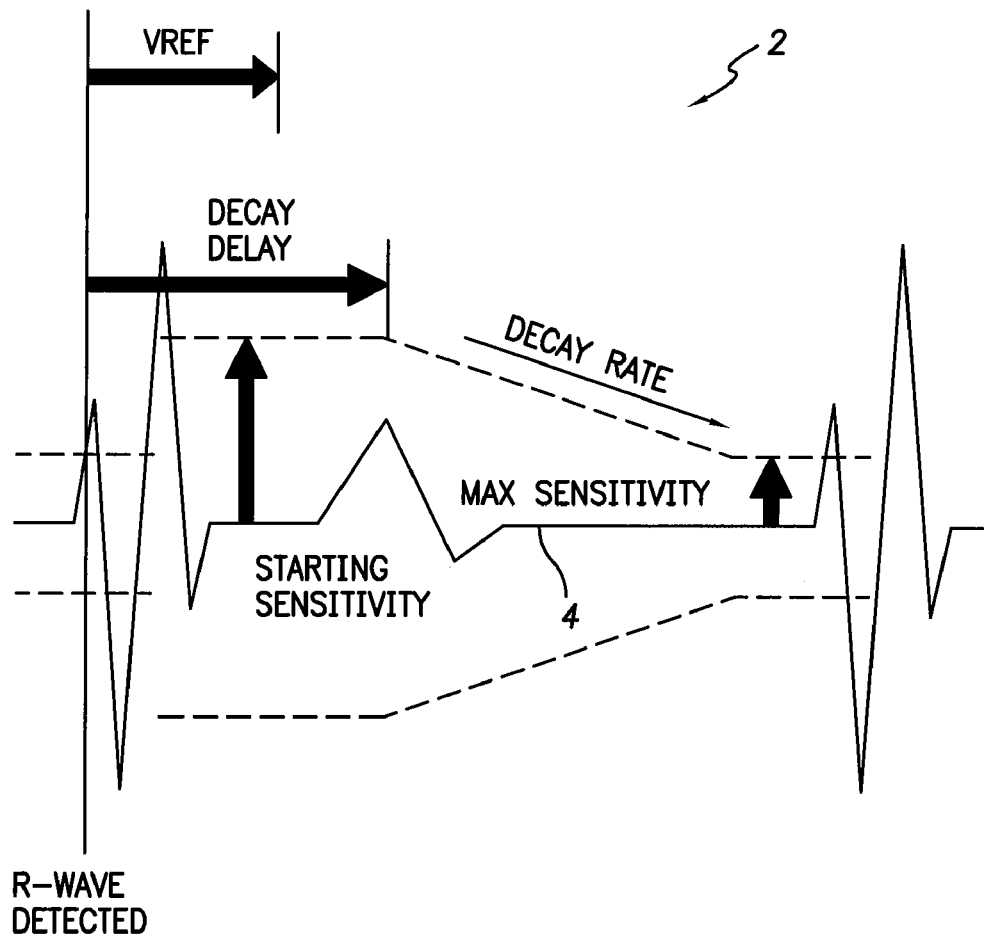
FIG. 1 is a graph illustrating exemplary conventional ventricular ASC parameters.
Figure 2:
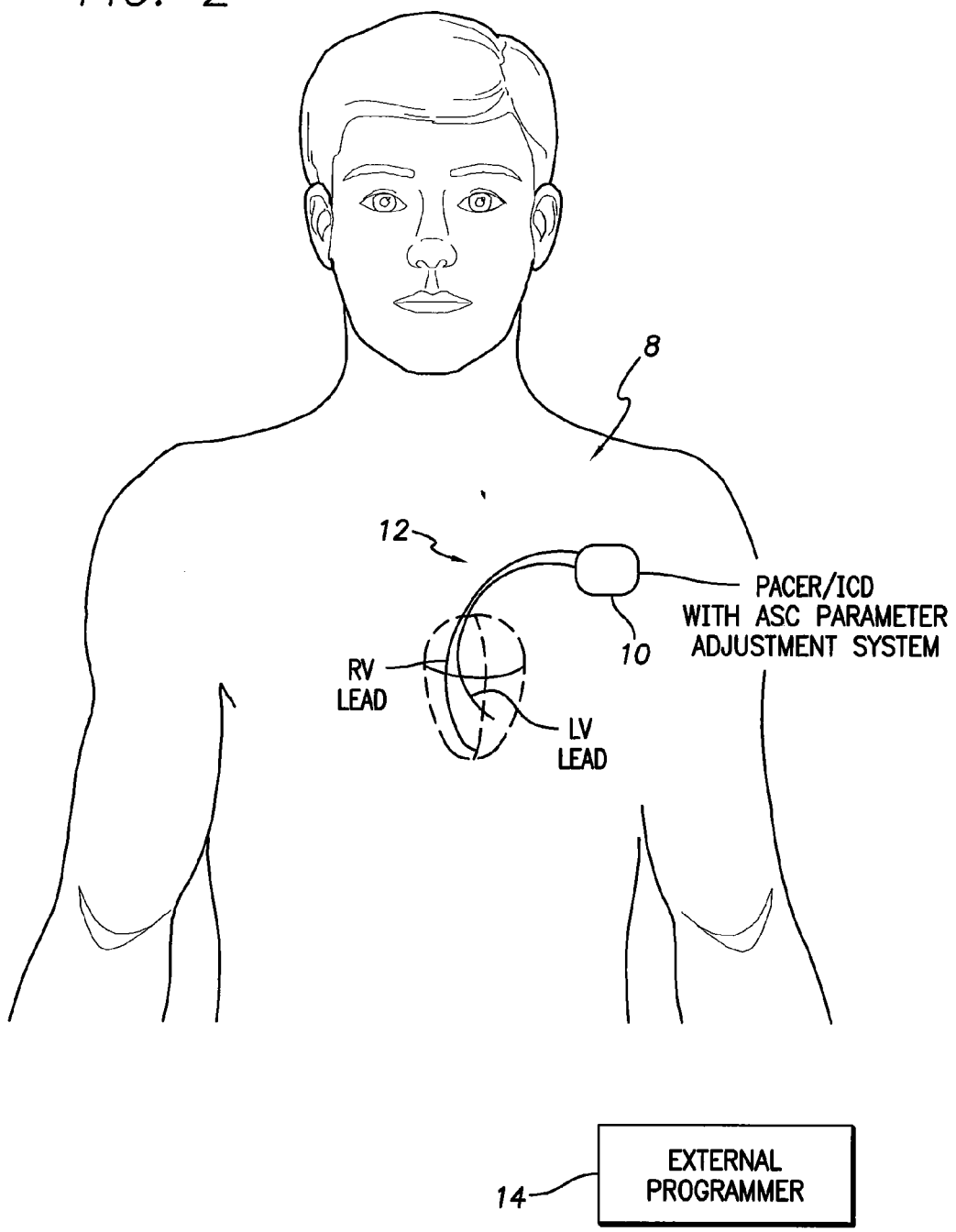
FIG. 2 illustrates pertinent components of an implantable medical system having a pacemaker or ICD equipped with an ASC parameter adjustment system.
Figure 19:
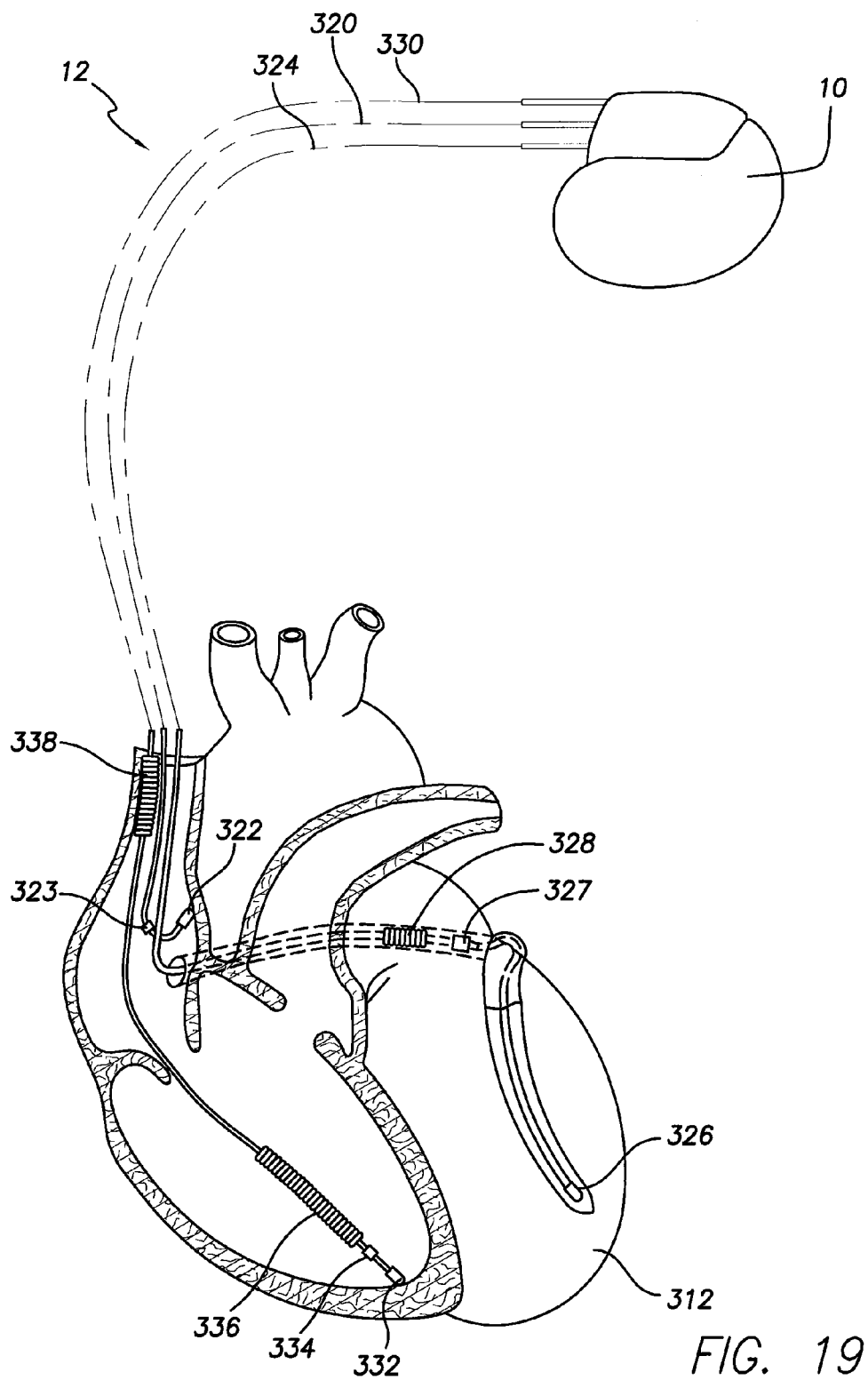
FIG. 19 is a simplified, partly cutaway view, illustrating the pacer/ICD of FIG. 2 along with a set of exemplary leads implanted in the heart of the patient.

FIG. 2 illustrates an implantable medical system 8 having a pacer/ICD 10 equipped with an on-board ASC parameter adjustment system operative to automatically adjust ASC parameters employed by the pacer/ICD, such as Starting Sensitivity; Decay Delay; Maximum Sensitivity; Refractory Interval; and Decay Rate. The ASC parameters are, in turn, used by the device to adjust the sensitivity by which the pacer/ICD senses electrical cardiac signals in the heart of the patient via leads 12. The leads are also used to deliver pacing pulses or other electrical stimulation. In FIG. 2, only two leads are shown; a complete set of leads is shown in FIG. 19 and described below. In the preferred implementation, the ASC parameters are initially programmed into the pacer/ICD by a clinician using an external programmer 14 following device implantation. The pacer/ICD then adjusts those parameters to account for changes in noise levels and other factors. Alternatively, however, the pacer/ICD can be equipped to also initially set the ASC parameters such that the clinician need not program the ASC parameters.

Although a pacer/ICD is illustrated in FIG. 2, it should be understood that the general reprogramming techniques of the invention may potentially be implemented within other implantable medical devices employing some sort of automatic sensitivity control procedure, such as device for sensing electrical signals in the brain or other organs. Note also that the particular size, shape and implant locations of the pacer/ICD and its leads are merely illustrative and do not necessarily correspond to actual sizes, shapes and locations, which may vary from patient to patient and may further vary depending upon the particular devices being implanted.

ASC Adjustment Based on Noise Floor and Feature Amplitudes

Figure 3:
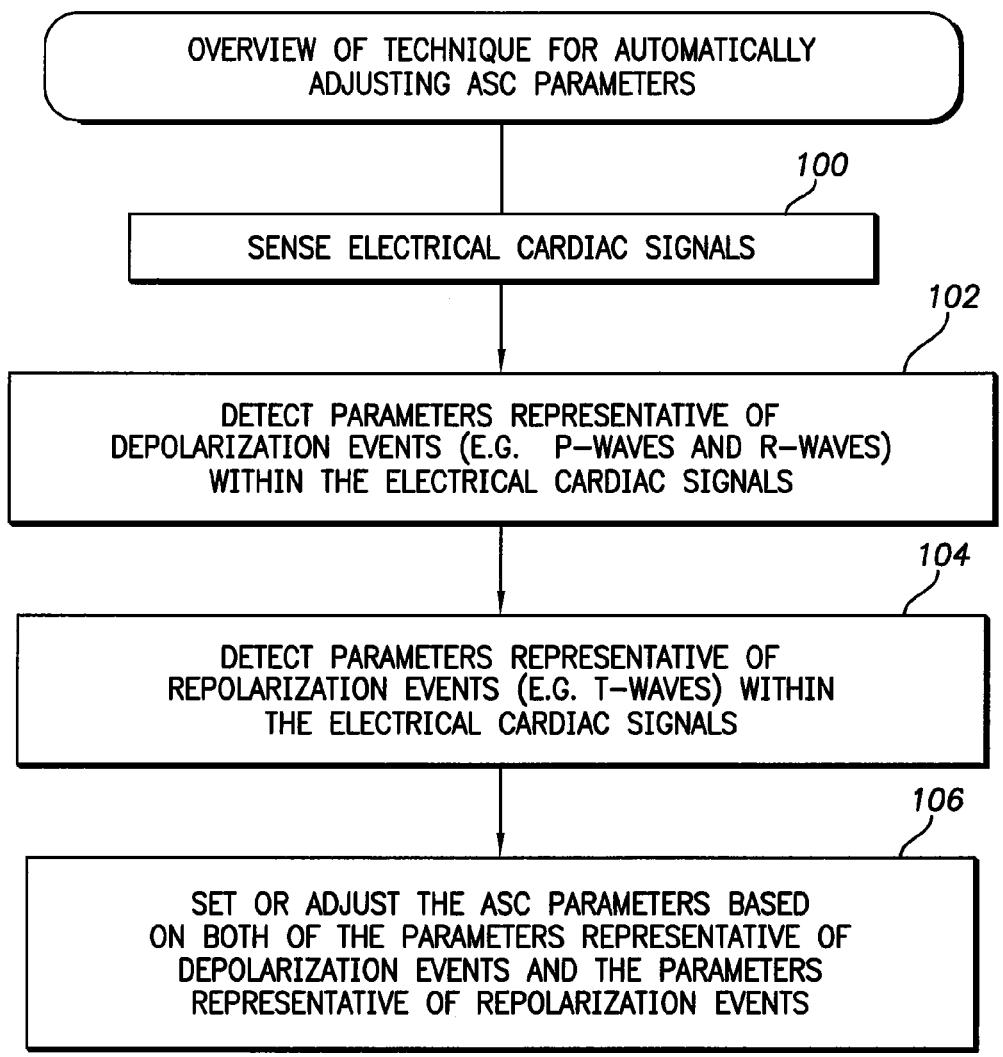
FIG. 3 provides an overview of a technique for automatically setting or adjusting ASC parameters based depolarization and repolarization event measurements, which may be performed by the implantable system of FIG. 2.

FIG. 3 provides an overview of a technique for adjusting ASC parameters based on noise measurements in combination with depolarization and repolarization signals amplitudes (i.e. P-wave, R-wave, and T-wave amplitudes.) Briefly, at step 100, the pacer/ICD senses electrical cardiac signals. At step 102, the pacer/ICD detects parameters representative of depolarization events (i.e., P-waves and R-waves) within the electrical cardiac signals. At step 104, the pacer/ICD detects parameters representative of repolarization events (i.e., T-waves) within the electrical cardiac signals. The detected parameters include one or more of: depolarization amplitudes (i.e. P-wave and/or R-wave amplitudes); repolarization amplitude (T-wave amplitude); depolarization widths (i.e. P-wave and/or R-wave widths); repolarization width (i.e. T-wave width); and intervals between depolarization and repolarization events (i.e. the RT interval or related intervals such as ST interval). On the atrial channel, it may be appropriate to also detect atrial repolarization parameters as well as the interval between the P-wave and the corresponding atrial repolarization event.

Otherwise conventional parameter detection or measurement techniques may be used at steps 102 and 104. However, insofar as the T-wave is concerned, the location and features of the T-wave are preferably measured using techniques set forth in: U.S. patent application Ser. No. 10/979,833, of Snell et al., entitled "Systems and Methods for Automatically Setting Refractory and Blanking Periods," filed Nov. 1, 2004. Techniques for detecting and measuring T-wave parameters are also discussed in: U.S. patent application Ser. No. 10/603,398, entitled "System And Method For Detecting Cardiac Ischemia Based On T-Waves Using An Implantable Medical Device," of Min et al., filed Jun. 24, 2003; U.S. Pat. Nos. 6,862,471 and 6,711,438 to McClure, et al. both entitled "Method and Apparatus for Blanking T-Waves from Combipolar Atrial Cardiac Signals based on Expected T-Wave Locations"; U.S. Pat. No. 6,650,931 to McClure, et al., entitled "System and Method of Automatically Determining the Onsets and Ends Of Cardiac Events and Far-Field Signals"; and U.S. patent application Ser. No. 11/394,724, of Ke et al., entitled "System And Method For Detecting Cardiac Ischemia In Real-Time Using A Pattern Classifier Implemented Within An Implantable Medical Device," filed Mar. 31, 2006.

At step 106, the pacer/ICD then sets or adjusts the ASC parameters based on the parameters representative of depolarization and repolarization events obtained at steps 102 and 104. Thus, ASC parameters are automatically set or adjusted by the device itself based on both depolarization parameters and repolarization parameters. In examples below, the adjustments also take into account detected noise parameters, such as a noise floor. The ASC parameters are adjusted so as to permit the actual sensitivity with which signals are sensed to be controlled so as to minimize the risk of over-sensing and under-sensing of the signals of interest, particularly R-waves on the ventricular channel and P-waves on the atrial channel. Numerous detailed examples are provided below.

Figure 4:
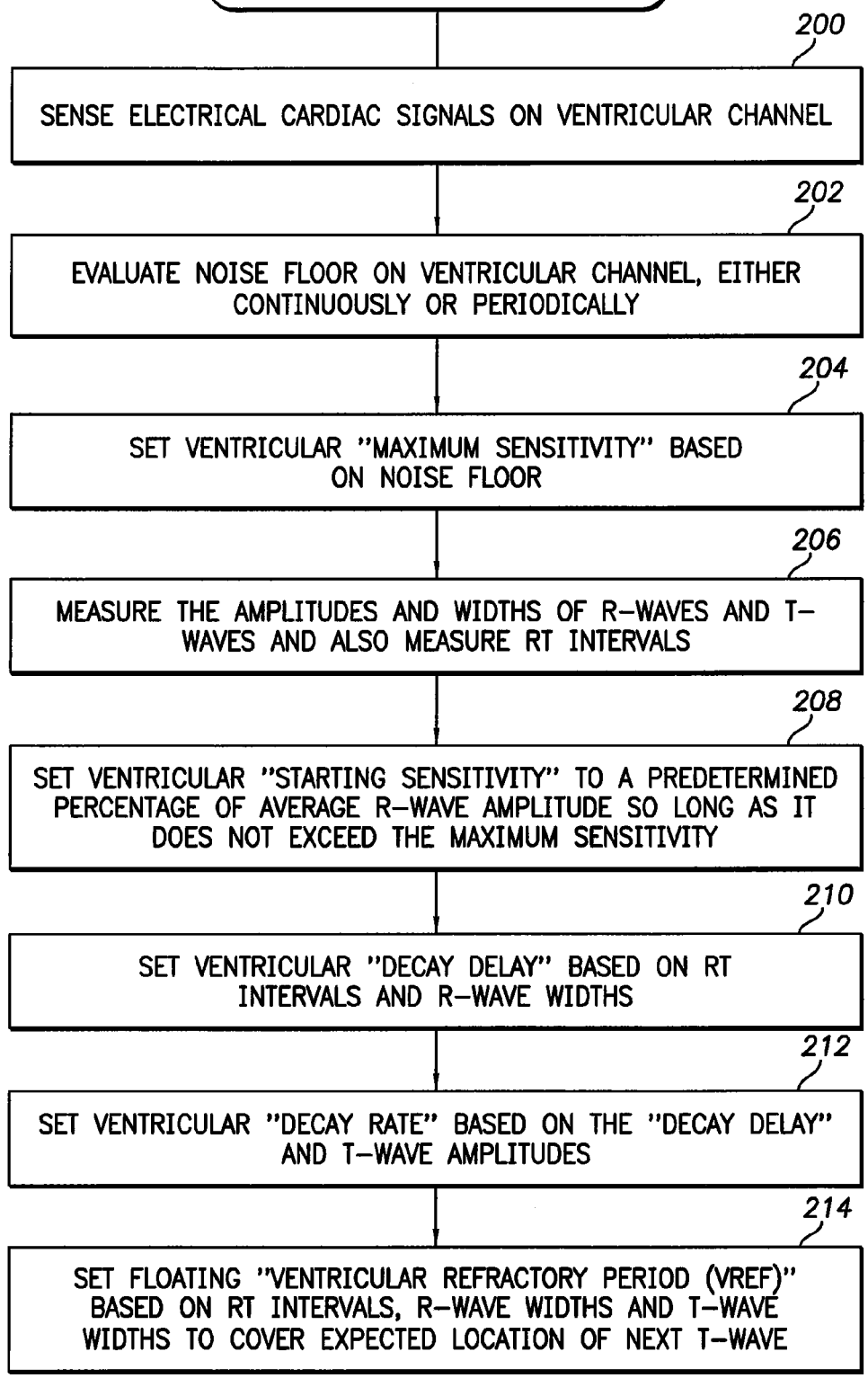
FIG. 4 is a flow chart summarizing an exemplary implementation of the technique of FIG. 3, particularly for use on a ventricular sensing channel.
Figure 5:
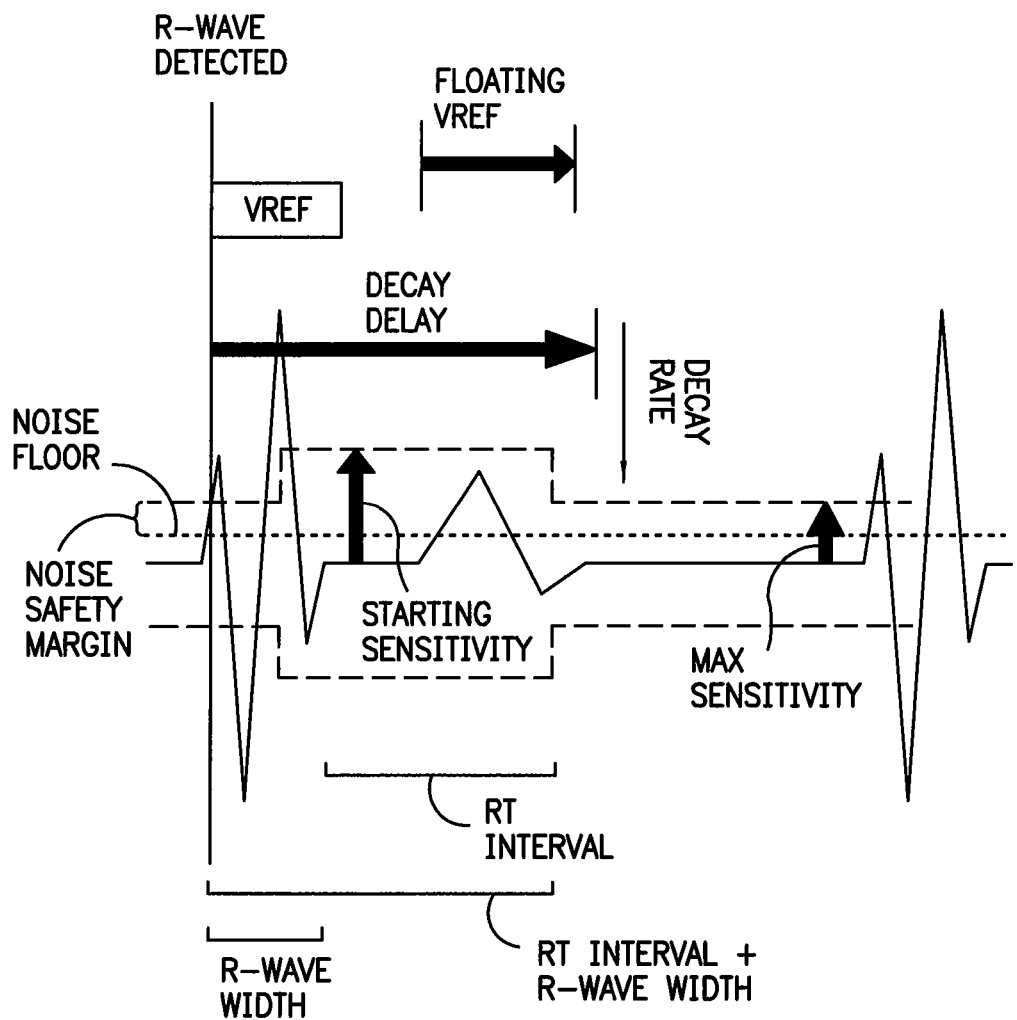
FIG. 5 is a graph illustrating exemplary ventricular ASC parameters specified in accordance with the technique of FIG. 4 wherein a floating refractory period is provided to cover the T-wave.

FIGS. 4 and 5 illustrate a ventricular channel example wherein signal noise is also taken into account. At step 200, the pacer/ICD senses electrical cardiac signals on a ventricular channel using a ventricular sense amplifier and, at step 202, the pacer/ICD evaluates the ventricular channel noise floor. In other examples, the noise floor is measured on both the atrial and ventricular channels. Otherwise conventional noise detection techniques may be employed. In particular, see techniques described in U.S. Pat. No. 6,321,115 to Mouchawar, et al., entitled "Noise Detection System and Method for use in an Implantable Medical Device" and U.S. Pat. No. 6,493,584 to Lu, entitled "Implantable Cardiac Stimulation Device and Method which Discriminates between Noise and Cardiac Activity." The patent applications to Linder et al., Wohlgemuth et al., Palreddy et al., cited above, also discuss noise detection. Depending on the implementation, the noise floor can be evaluated either continuously or periodically. By continuously, it is meant that the noise evaluation occurs substantially in real time, such as once per cardiac cycle. By periodically, it is meant that the noise evaluation is performed less frequently, such as once per hour or perhaps once per day. The noise floor may be represented as an mV value, representative of the effective voltage level of the noise. At step 204, the pacer/ICD sets the ventricular Maximum Sensitivity parameter based on the noise floor. In the example of FIG. 5, the Maximum Sensitivity is set by adding a predetermined safety margin mV value to the mV value of the noise floor. In other examples, the noise floor mV value is multiplied by a predetermined safety margin factor, such as by a factor of two.

At step 206, the pacer/ICD measures the amplitudes and widths of R-waves and T-waves on the ventricular channel and also measures RT intervals. In one example, each sensed R-wave and T-wave is analyzed to determine its peak amplitude and its width. Note here that, although the T-wave is not detected for the purposes of triggering/inhibiting pacing therapy, it is nevertheless sensed for the purposes of setting the ASC parameters. In this regard, the ASC sensing thresholds are "software" thresholds, not "hardware" thresholds. Highly sensitive thresholds are applied to the sensed IEGM signal to identify the T-wave. The T-wave is then analyzed to extract its peak amplitude and width, as well as to measure the RT interval (or other appropriate parameter such as the ST interval).

At step 208, the pacer/ICD then sets the "Starting Sensitivity" of the ventricular channel to a predetermined percentage of the latest R-wave amplitude so long as it does not exceed the maximum sensitivity (i.e. so long as the mV value of Starting Sensitivity is not less than the mV value of Maximum Sensitivity.) The percentage may be a pre-programmed value, such as the example of FIG. 5 wherein the Starting Sensitivity is set to 50% of the R-wave peak amplitude. In other examples to be described below, the percentage is set based on the relative sizes of the R-wave and T-wave. In this regard, if the T-wave is typically larger than the R-wave, the Starting Sensitivity mV value is preferably set high larger than the R-wave amplitude so that it will likewise be higher than the T-wave amplitude, thus preventing the T-wave from being inadvertently sensed. Hence, the Starting Sensitivity is dependent, at least, upon the amplitude of the current R-wave and on the current Maximum Sensitivity (which is in turn dependent upon the noise floor) and may be dependent upon other factors as well, including the T-wave. At step 210, the pacer/ICD then sets the "Decay Delay" of the ventricular channel based on the latest RT intervals and R-wave widths measured at step 206. In the example of FIG. 5, the Decay Delay is set equal to the RT interval plus the R-wave width. The RT interval plus the R-wave width is used here as an estimate of the expected location of the end of the T-wave. With the Decay Delay set accordingly, the sensitivity will thereby remain at the Starting Sensitivity value until after the T-wave is substantially complete, thereby helping to ensure that the T-wave will not be inappropriately sensed and misinterpreted as an R-wave.

At step 212, the pacer/ICD sets the Decay Rate based on the Decay Delay and, in some examples, based on the latest measured T-wave amplitudes. In the example of FIG. 5 where the Decay Delay is set to expire after the T-wave completes, the Decay Rate is preferably set to its maximum programmable value to permit the sensitivity to be increased as quickly as possible. Ideally, the Decay Rate is set to cause the sensitivity to immediately jump to the Maximum Sensitivity upon completion of the Decay Delay, as shown in FIG. 5. This is permissible since the T-wave has substantially elapsed before the sensitivity is increased. In examples where the Decay Delay is instead set to expire well before the end of the T-wave, the Decay Rate is set to cause the sensitivity mV value to increase at a generally slower rate set so that the sensitivity does not reach the Maximum Sensitivity until after the expected end of the T-wave. At step 214, the pacer/ICD sets a floating "ventricular refractory period (VREF)" based on the expected RT interval, R-wave width and T-wave width to cover expected location of the next T-wave (again see FIG. 5). The floating VREF is in addition to a fixed VREF that commences upon detection of the R-wave and has a length set based on the expected width of the R-wave.

Figure 6:
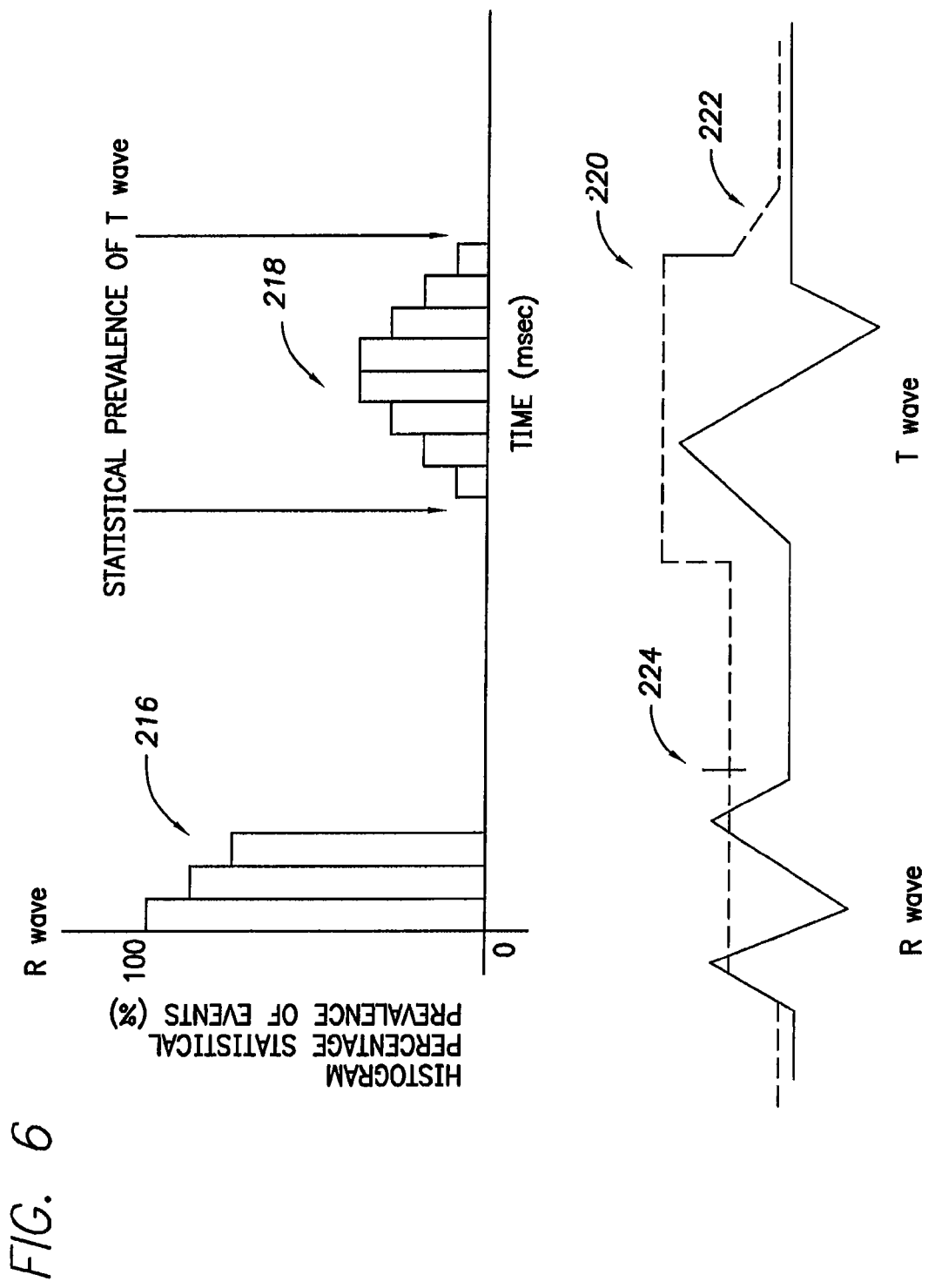
FIG. 6 is a graph illustrating exemplary histograms for use in determining the expected location and width of the R-wave and the T-wave for use with the technique of FIG. 3, wherein an adjustable sensitivity profile is used instead of a floating refractory period.
Figure 7:
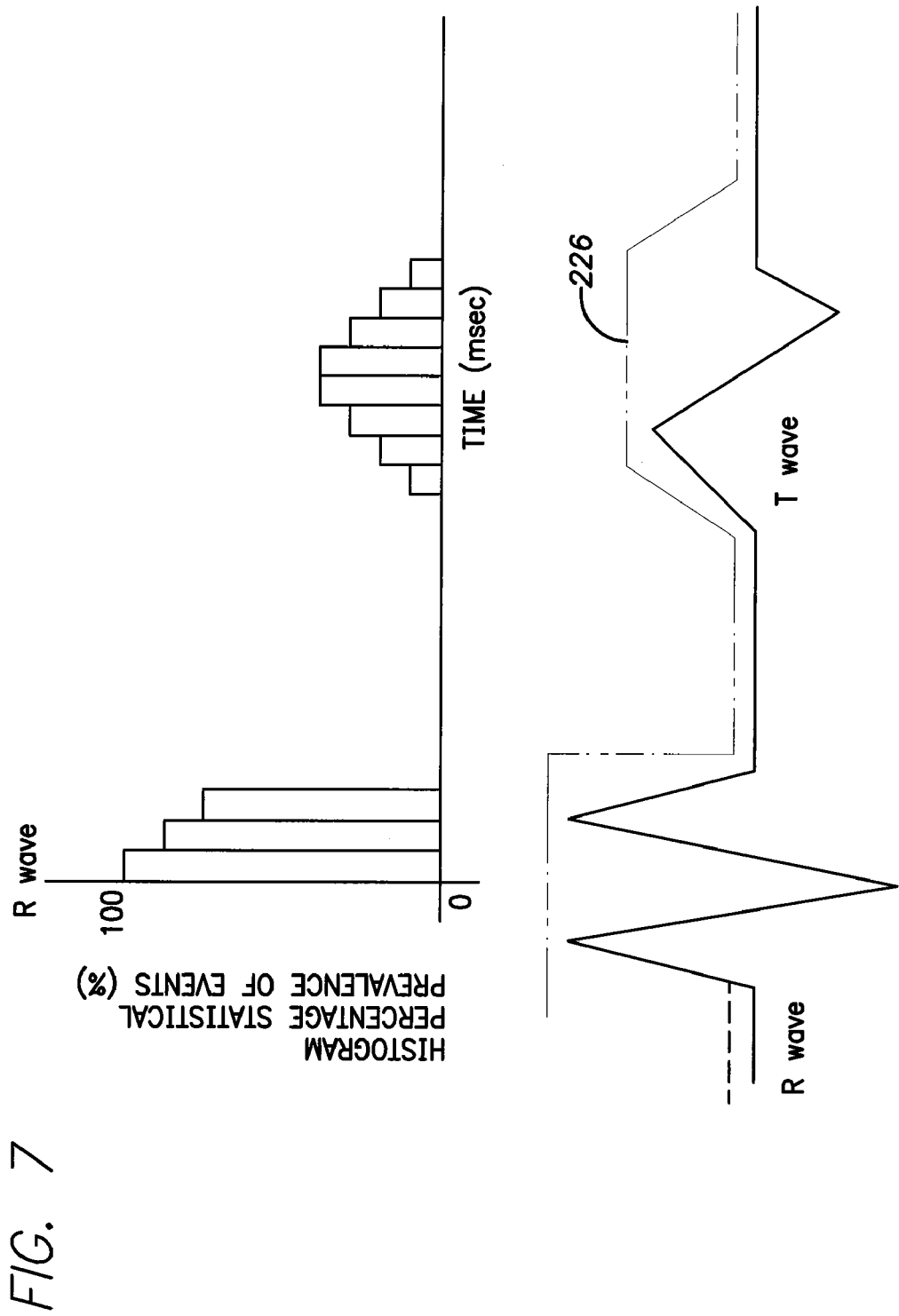
FIG. 7 is another graph illustrating exemplary histograms and an adjustable sensitivity profile.
Figure 8:
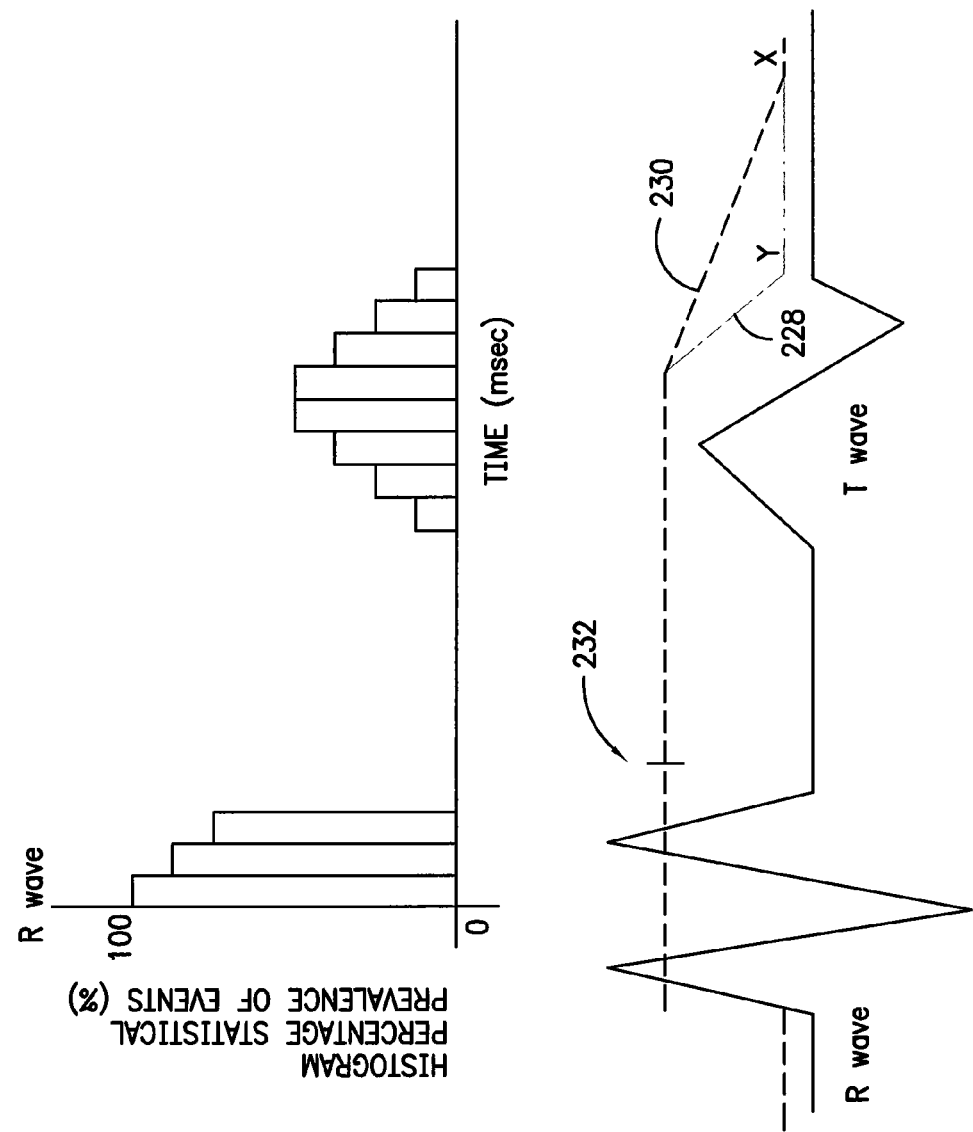
FIG. 8 is yet another graph illustrating exemplary histograms for, but wherein Decay Rate is adjusted based on T-wave location and width.

Turning now to FIGS. 6-8, alternatives are illustrated where a floating VREF is not used. These figures also illustrate the use of histograms to determine the width of the R-wave and the location and width of the T-wave. The histograms represent the statistical prevalence of R-width and T-wave location and width. That is, whenever R-waves and T-waves are detected, appropriate histogram bins are incremented to record the location and width of these features. See, the patent application of Snell et al. cited above for information on suitable techniques for generating and updating histograms representative of features of electrical cardiac signals. As shown in FIG. 6, preferably, separate histograms 216 and 218 are maintained for the R-wave and for the T-wave. In the case of the R-wave, histogram 216 only tracks the second half of the R-wave, i.e. it only tracks the portion of the R-wave following its peak. Hence, R-wave histogram 216 tracks the statistical prevalence of the width of the histogram. In the case of the T-wave, histogram 218 tracks the entire T-wave. Hence, the T-wave histogram tracks the statistical prevalence of both the location of the T-wave (relative to the peak of the R-wave) as well as the width of the histogram. Based on the statistical prevalence of these features, the pacer/ICD then adjusts the ventricular sensitivity so as to avoid T-wave oversensing, with the adjustment represented in the figure by way of dashed line 220 indicated the sensitivity mV value. Note that, in this example, the sensitivity mV value increases sharply prior to the T-wave and then decreases sharply back down to its previous level following the T-wave. Thereafter, the sensitivity mV value decrease gradually and linearly in accordance with a decay rate value during time 222. Also, in this example, a fixed VREF is also used that covers the R-wave and prevents double counting of the R-wave itself. The end point 224 of the fixed VREF covering the R-wave is identified in the figure. Typically, the VREF is about 100 ms in duration.

FIG. 7 illustrates another example involving the use of histograms. Again, the histograms represent the statistical prevalence of R-width and T-wave location and width. In this example, however, a sensitivity profile 226 is generated based on the relative widths and locations of the R-wave and T-wave (as determined based on the statistical prevalence histograms.) No VREFs are provided, floating or otherwise. Insofar as the R-wave is concerned, the sensitivity mV value is kept high enough to avoid double counting of the R-wave. The sensitivity mV value then drops sharply following the expected end of the R-wave. Insofar as the T-wave is concerned, the sensitivity mV value increases gradually prior to the expected beginning of the T-wave and then decreases gradually following the expected end of the T-wave. In one example, the starting sensitivity may be set to 70% of the R-wave amplitude. The Decay Delay may be set to 40 ms.

FIG. 8 illustrates yet another example involving the use of histograms. Again no floating VREF is used; nor is an adjustable T-wave profile employed (as with FIGS. 6 and 7). Rather, otherwise standard ASC parameters are employed. However, the decay rate is set by the pacer/ICD based on the expected width and location of the T-wave (as derived from the statistical prevalence histograms) so as to avoid over-sensing the T-wave. That is, if the T-wave is expected to be relatively short, the decay rate is set to be relatively quick 228, so that the sensitivity mV value drops to the mV level of maximum sensitivity at time Y. If the T-wave is expected to be relatively long, the decay rate is set to be relatively slow 230, so that the sensitivity mV value does not drop to the mV level of maximum sensitivity until time X. In this example, a VREF is provided over the R-wave, ending at time 232 to avoid doubled sensing of the R-wave.

Figure 9:
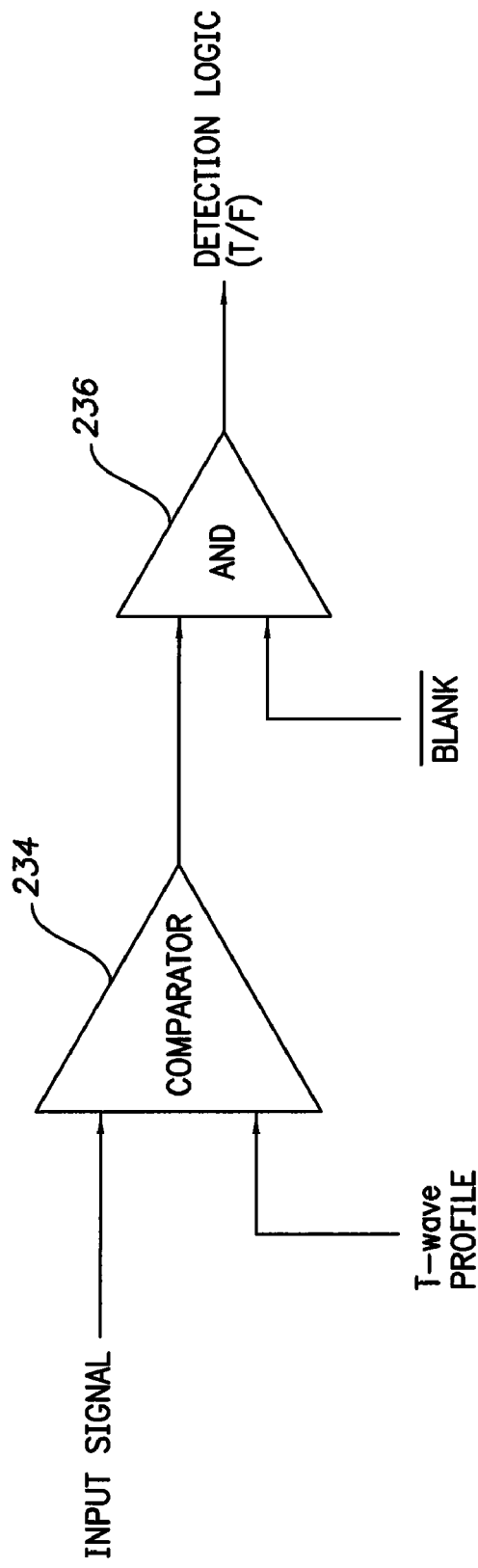
FIG. 9 is a circuit schematic illustrating detection logic that may be exploited by the technique of FIG. 3 when using a floating refractory interval.

FIG. 9 is a schematic illustrating detection logic that may be exploited by the technique of FIG. 3 when using a floating refractory interval. A comparator 234 and an AND gate 236 are employed. The comparator receives both the input ventricular channel signal as well as a T-wave profile (in the form of an ensemble averaged envelope based on historical T-wave morphologies.) The output of the comparator is applied to a first input of the AND gate. The second input of the AND gate receives a NOT BLANK signal. The output of the AND gate is forwarded to detection circuitry. Briefly, the input signal may be a time-varying IEGM signal, such as a V-IEGM, synchronized to an R-wave or V-pulse. The T-wave profile is a time-varying signal representative of the profile of a T-wave. At any point in time when the IEGM signal exceeds the T-wave profile, the comparator outputs a TRUE output (i.e. a "1"). Otherwise, comparator outputs a FALSE output (i.e. a "0"). In other words, the output of the comparator remains FALSE so long as the IEGM signal remains below (or within) the T-wave envelope. This is the typical case. If the output of the comparator is ever TRUE, that is an indication of an abnormal event, i.e. it is an indication that something other than a T-wave is appearing in the IEGM signal during the period of time when a T-wave is expected. On the V-IEGM channel, this anomalous event may be another R-wave appearing when the T-wave is expected. On the A-IEGM signal, the anomalous event may be a P-wave appearing when a far-field T-wave is expected. Downstream detection logic responds to the detection of the abnormal event by analyzing the event to identify it so that appropriate action can be taken. Thus, rather than blanking the input signal throughout the expected location of the T-wave (and thereby also blanking any other events occurring at the same time), the circuit of FIG. 9 instead allows non-T-wave events to still be detected during the T-wave, so long as they exceed the T-wave profile at some point. Note that blank signal provided to the AND gate is employed to gate the final output so as to ensure the output is always FALSE in circumstances where the output signal is unnecessary or would be unreliable. For example, a detection circuit on an atrial channel may be turned off during atrial fibrillation by using the blank signal. The circuit schematic of FIG. 9 may be implemented in software using a data comparator. Alternatively, it may be implemented as a hardwired circuit. Typically, separate circuits are provided on the separate channels, e.g. separate A-IEGM and V-IEGM circuits, etc.

Figures 1, 10:
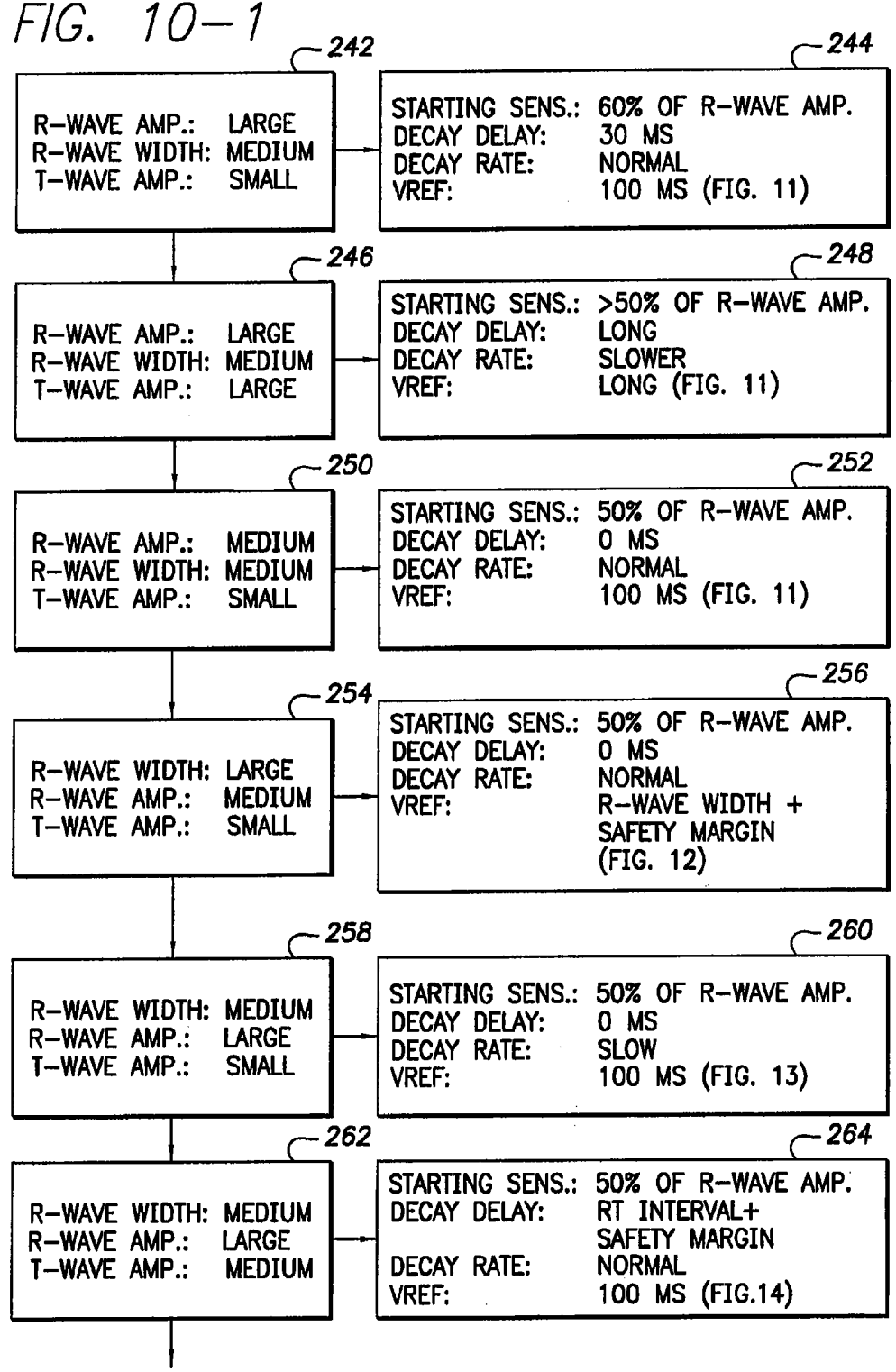
FIG. 10 is a flow chart summarizing another exemplary implementation of the technique of FIG. 3, wherein specific ASC parameter adjustment procedures are performed based on the relative sizes of the R-wave and T-wave.
Figures 2, 10:
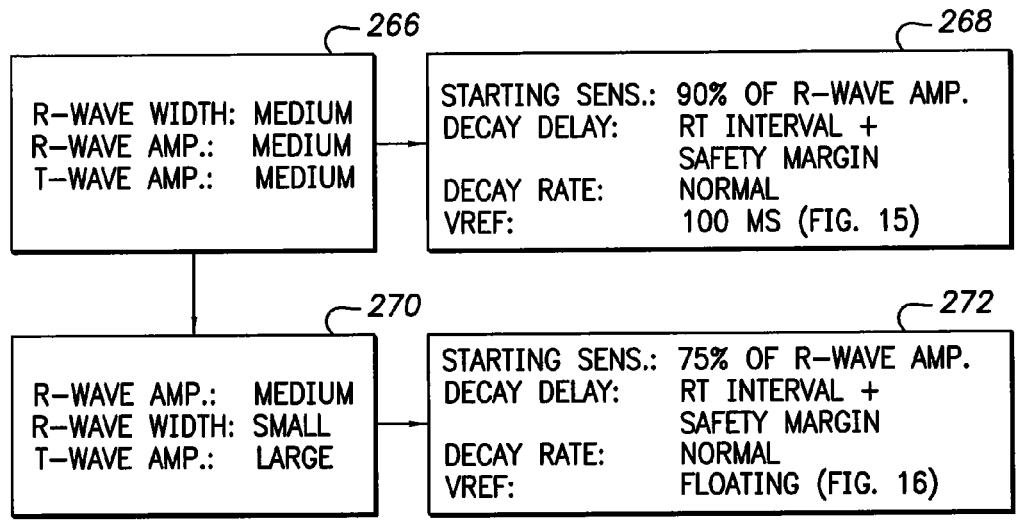

Turning now to FIGS. 10-18, various specific examples will be described wherein the pacer/ICD sets the ASC parameters based on the relative sizes and widths of the R-wave and the T-wave so as to avoid double sensing while still permitting signals of interest to be detected. FIG. 10 summarizes exemplary decision logic. FIGS. 11-18 illustrated various exemplary cases.

Figure 11:
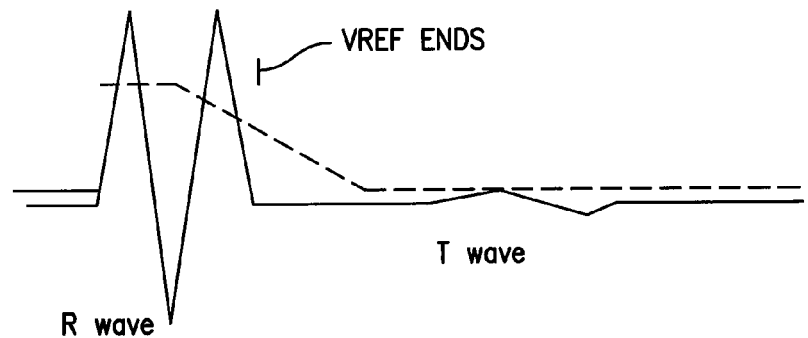
FIG. 11 is a graph illustrating a cardiac signal having a large R-wave and minimal T-wave processed by the technique of FIG. 10.

Referring first to FIG. 10, if at step 242 the amplitude of the R-wave is large i.e. larger than nominal but has normal width (as predicted based on statistical prevalence) whereas the T-wave amplitude is expected to be small (as also predicted based on statistical prevalence), then step 244 is performed wherein: the ASC parameters are all set to nominal values. Exemplary nominal values are: 60% of R-wave amp.; Decay Delay is set to 30 ms; the Decay Rate is set to a normal or nominal value; and a VREF of 100 ms is applied following the detection point of the R-wave. This is illustrated in FIG. 11. In this case, since the R-wave has much greater amplitude that the T-wave, nominal ASC parameters may be used (typically the original parameters programmed in the device by the physician) without further adjustment. Note that, with a Decay Delay of only 30 ms, the sensitivity may being begin to increase immediately during the R-wave. This is not a problem since a VREF is used to exclude the R-wave and so the sensitivity mV value can be below the R-wave amplitude during that interval. A standard length VREF is employed since the R-wave is not unusually wide. To determine whether the R-wave and T-wave parameters match the conditions of step 242, the expected value of the parameters (derived from statistical prevalence) may be compared again suitable thresholds.

Figure 12:
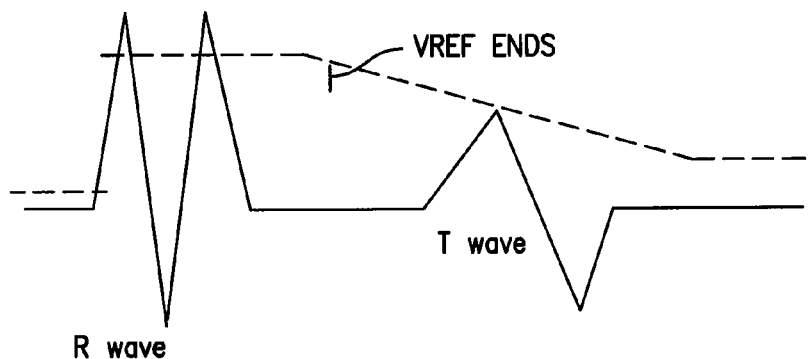
FIG. 12 is a graph illustrating a cardiac signal having both a large R-wave and a large T-wave processed by the technique of FIG. 10.

Referring again to FIG. 10, if at step 246 the amplitude of the R-wave is large (but of normal width) and the T-wave amplitude is also expected to be large, then step 248 is performed wherein some combination of the following parameters are employed by the ASC to avoid over-sensing of the T-wave: the Starting Sensitivity is set higher than its nominal value; the Decay Delay is set to be longer than nominal; and a longer VREF is used. A slower Decay Delay may also be employed. This is illustrated in FIG. 12. In this case, since the T-wave also has a large amplitude, nominal ASC parameters are not used. Rather, the parameters are modified to cause the sensitivity mV value to begin decreasing later and more slowly so that it remains above the mV value of the T-wave.

Figure 13:
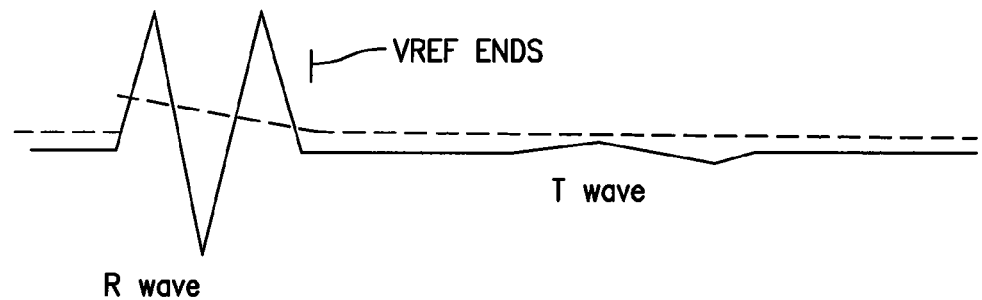
FIG. 13 is a graph illustrating a cardiac signal having a minimal T-wave processed by the technique of FIG. 10.

If at step 250 of FIG. 10, the width and amplitude of the R-wave is expected to be medium i.e. nominal (as predicted based on statistical prevalence) whereas the T-wave amplitude is expected to be small (as also predicted based on statistical prevalence), then step 252 is performed wherein: the Starting Sensitivity is set to 50% of R-wave amp.; the Decay Delay is set to 0 ms; the Decay Rate is set to a normal or nominal value; and a VREF of 100 ms is applied following the detection point of the R-wave. This is illustrated in FIG. 13. In this case, since the T-wave is small (or non-existent), a relatively low starting sensitivity may be used. Also, the sensitivity may start to gradually increase immediately following detection of the R-wave since, again, the T-wave is small and hence there is no significant risk that the T-wave will be inadvertently sensed. (Also, since a VREF is used to exclude the R-wave, the sensitivity can be below the R-wave amplitude during the VREF.) A standard length VREF is employed since the R-wave is not unusually wide. To determine whether the R-wave parameters are nominal, the expected R-wave width and amplitude may be compared again suitable thresholds. Likewise, the expected T-wave amplitude may be compared against a suitable threshold to determine whether is should be deemed to be small.

Figure 14:
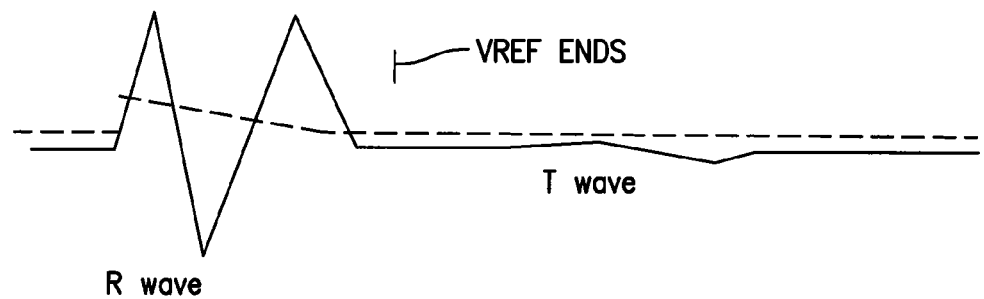
FIG. 14 is a graph illustrating a cardiac signal having a wide R-wave processed by the technique of FIG. 10.

If, at step 254 of FIG. 10, the expected R-wave width is instead found to be larger than normal (while the R-wave amplitude is still medium and the T-wave size is still small), then step 256 is performed wherein: the Starting Sensitivity is again set to 50% of R-wave amp.; the Decay Delay is again set to 0 ms; and the Decay Rate is again set to a normal or nominal value. However, the VREF is set based on the expected width of the R-wave plus a predetermined safety margin. This is illustrated in FIG. 14. In this case, since the R-wave is wider than normal, a longer VREF is used.

Figure 15:
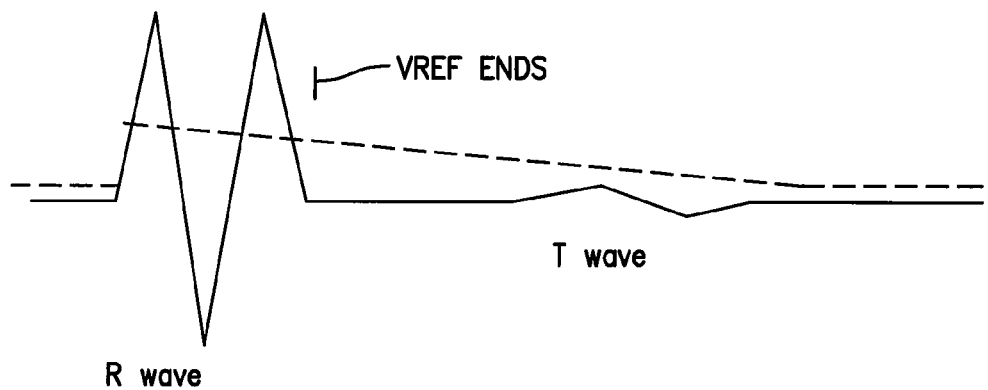
FIG. 15 is a graph illustrating a cardiac signal also having a large R-wave and a small T-wave processed by the technique of FIG. 10.

If, at step 258 of FIG. 10, the expected R-wave amplitude is instead found to be larger than normal (while the R-wave width is medium and the T-wave size is still small), then step 260 is performed wherein: the Starting Sensitivity is again set to 50% of R-wave amp.; the Decay Delay is again set to 0 ms; and the Decay Rate is set to be slower than normal. A VREF is set to 100 ms. This is illustrated in FIG. 15. In this case, since the R-wave is larger than normal, a slower decay is used.

Figure 16:
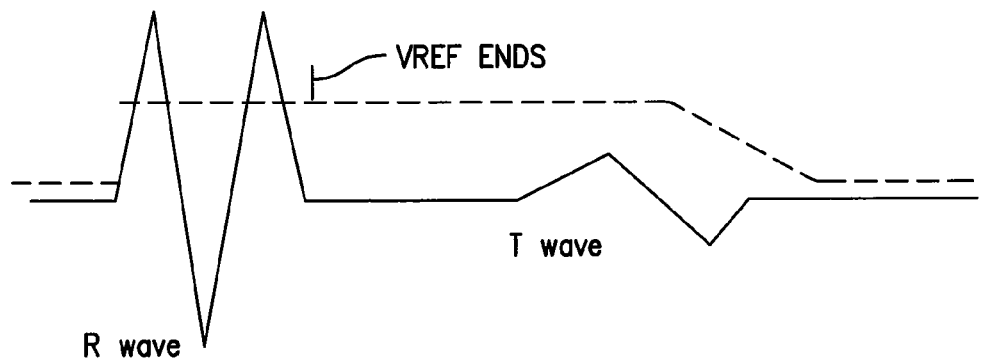
FIG. 16 is a graph illustrating a cardiac signal having a large R-wave but a normal T-wave processed by the technique of FIG. 10.

If, at step 262 of FIG. 10, the expected T-wave amplitude is instead found to be normal (while the R-wave width is medium and the R-wave amplitude is again larger than normal), then step 264 is performed wherein: the Starting Sensitivity is again set to 50% of R-wave amplitude and the Decay Rate is set to be normal. However, the Decay Delay is set to be equal to the expected RT interval plus a safety margin. A VREF is set to 100 ms. This is illustrated in FIG. 16. In this case, since the T-wave is normal, a Decay Delay set based on the RT interval is used to avoid T-wave over-sensing. The Starting Sensitivity may be set to 50% of R-wave amplitude since the R-wave amplitude is large.

Figure 17:
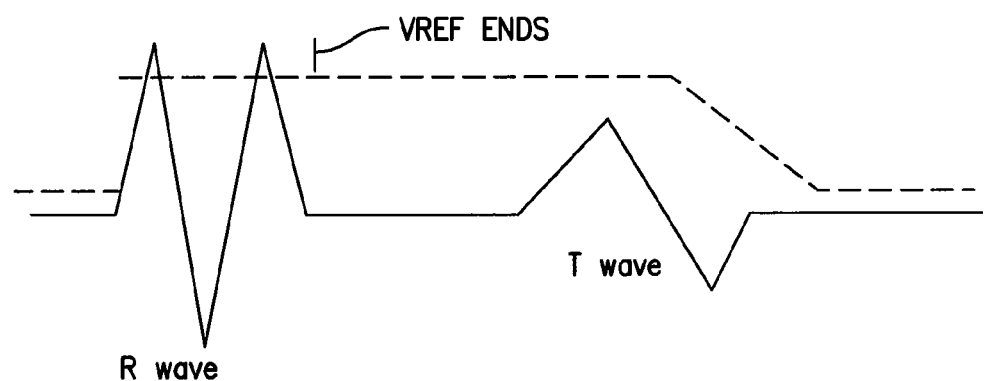
FIG. 17 is a graph illustrating a cardiac signal also having normal R-wave and T-wave sizes processed by the technique of FIG. 10.

If, at step 266 of FIG. 10, all R-wave and T-wave parameters are instead found to normal, then step 268 is performed wherein: the Starting Sensitivity is instead set to 90% of R-wave amplitude and the Decay Rate is set to be normal. However, the Decay Delay is set to be equal to the expected RT interval plus a safety margin. A VREF is set to 100 ms. This is illustrated in FIG. 17. In this case, since all parameters are normal, the Starting Sensitivity is set higher than usual (i.e. to 90% of R-wave amplitude) to help avoid T-wave over-sensing.

Figure 18:
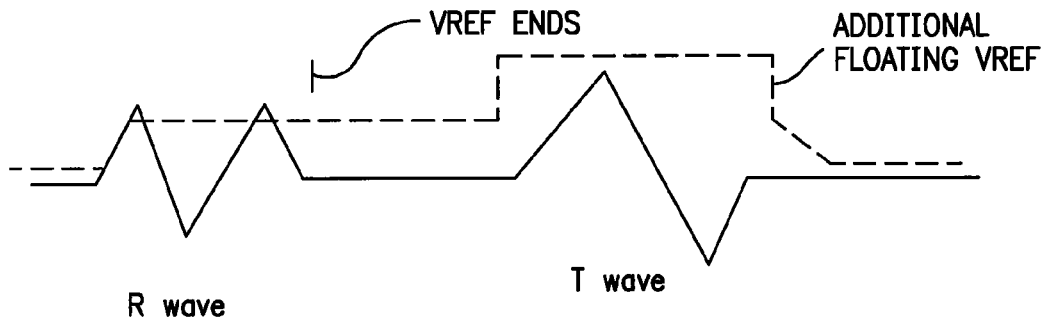
FIG. 18 is a graph illustrating a cardiac signal having large T-wave and a small R-wave processed by the technique of FIG. 10.

If, at step 270 of FIG. 10, the R-wave width is small, the R-wave amplitude is normal, and the T-wave amplitude is larger than normal, then step 272 is performed wherein: the Starting Sensitivity is instead set to 75% of R-wave amplitude and the Decay Rate is set to be normal. However, the Decay Delay is set to be equal to the expected RT interval plus a safety margin. A normal VREF is used that is set to 100 ms. An additional floating VREF is employed. This is illustrated in FIG. 18. In this case, since the T-wave is bigger than the R-wave, the floating VREF is used to help avoid T-wave over-sensing. As already explained in connection with FIG. 7, an adjustable Decay Rate may be advantageously used in some cases. Also, as explained in connection with FIG. 8, a sensitivity profile may be used in some cases. A similar technique to that of FIG. 10 may be applied to atrial channel signals.

What have been described are various techniques for automatically adjusting ASC parameters. For the sake of completeness, a detailed description of an exemplary pacer/ICD and an external programmer for performing these functions will now be provided. However, principles of invention may be implemented within other pacer/ICD implementations or within other external devices.

Exemplary Pacer/ICD

FIG. 19 provides a simplified diagram of a pacer/ICD, which is a multi-chamber stimulation device capable of treating both fast and slow arrhythmias with stimulation therapy, including cardioversion, defibrillation, and pacing stimulation. To provide atrial chamber pacing stimulation and sensing, pacer/ICD 10 is shown in electrical communication with a heart 312 by way of a right atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. (For pacer implementations without cardioversion/defibrillation, coils are not used.) Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 324 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 324 is designed to receive atrial and ventricular cardiac signals and to deliver left ventricular pacing therapy using at least a left ventricular tip electrode 326, left atrial pacing therapy using at least a left atrial tip electrode 327, and shocking therapy using at least a left atrial coil electrode 328. With this configuration, biventricular pacing can be performed. Although three leads are shown in FIG. 19, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 20:
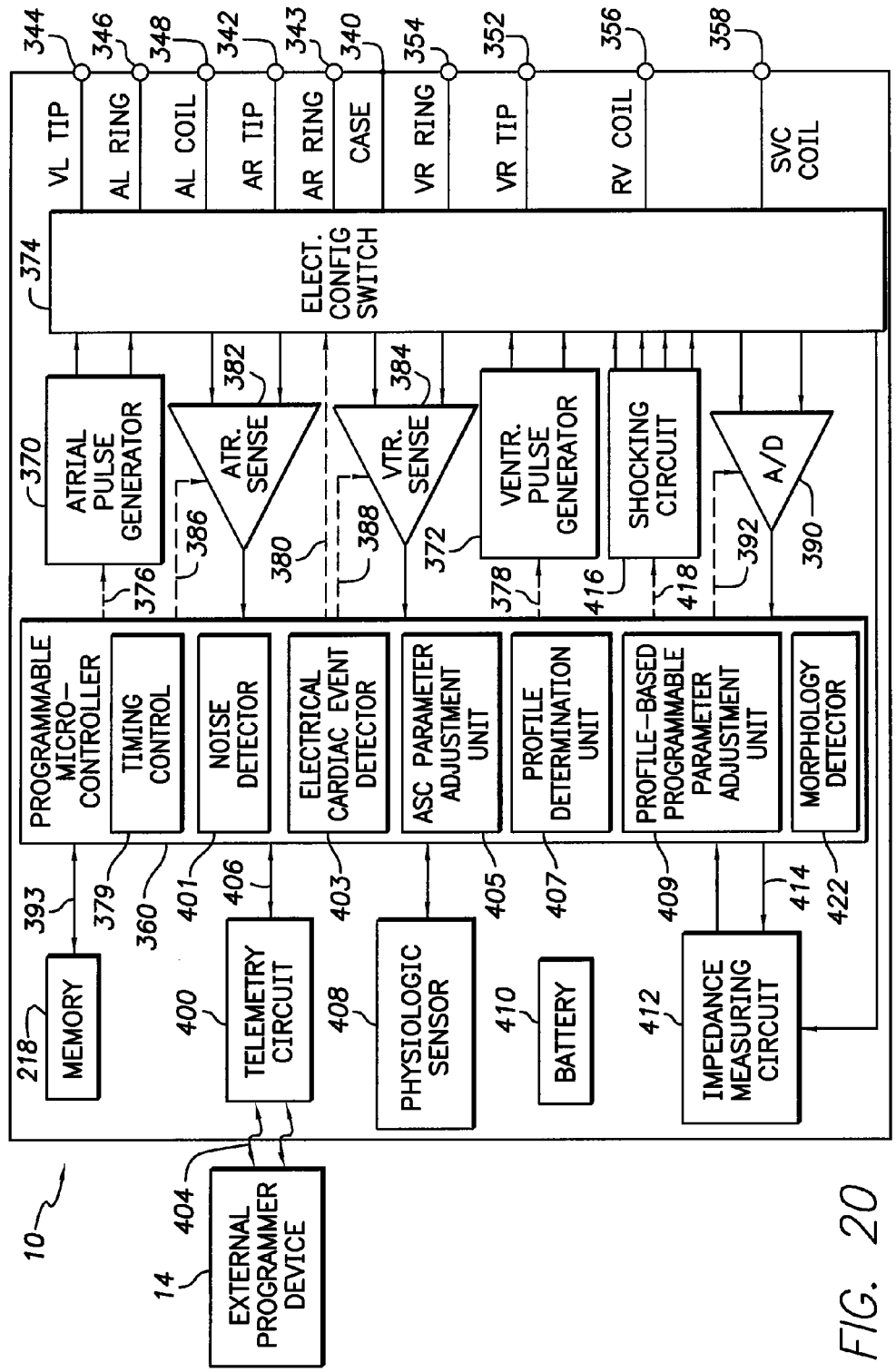
FIG. 20 is a functional block diagram of the pacer/ICD of FIG. 19, illustrating basic circuit elements that provide cardioversion, defibrillation and/or pacing stimulation in the heart and particularly illustrating an on-board ASC parameter adjustment system.

A simplified block diagram of internal components of pacer/ICD 10 is shown in FIG. 20. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for pacer/ICD 10, shown schematically in FIG. 20 is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338 (shown in FIG. 19), for shocking purposes. The housing 340 further includes a connector (not shown) having a plurality of terminals, 342, 343, 344, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes at least a left ventricular tip terminal ($V_L$ TIP) 344, a left atrial tip terminal ($A_L$ TIP) 346, and a left atrial shocking terminal ($A_L$ COIL) 348, which are adapted for connection to the left ventricular tip electrode 326, the left atrial ring electrode 327, and the left atrial coil electrode 328, respectively. To support right ventricular sensing, pacing and shocking, the connector further includes a right ventricular tip terminal ($V_R$ TIP) 352, a right ventricular ring terminal ($V_R$ RING) 354, a right ventricular shocking terminal ($R_V$ COIL) 356, and an SVC shocking terminal (SVC COIL) 358, which are adapted for connection to the right ventricular tip electrode 332, right ventricular ring electrode 334, the RV coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 20 an atrial pulse generator 370 and a ventricular pulse generator 372 generate pacing stimulation pulses for delivery by the right atrial lead 320, the right ventricular lead 330, and/or the coronary sinus lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, ER windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art.

Atrial sensing circuits 382 and ventricular sensing circuits 384 may also be selectively coupled to the right atrial lead 320, coronary sinus lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and automatic sensitivity control (ASC), bandpass filtering, and a threshold detection circuit, as known in the art, to selectively sense the cardiac signal of interest. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 390. The data acquisition system 390 is configured to acquire intracardiac electrogram signals, convert the raw analog data into a digital signal, and store the digital signals for later processing and/or telemetric transmission to an external device 12. The data acquisition system 390 is coupled to the right atrial lead 320, the coronary sinus lead 324, and the right ventricular lead 330 through the switch 374 to sample cardiac signals across any pair of desired electrodes. The microcontroller 360 is further coupled to a memory 218 by a suitable data/address bus 393 wherein the programmable operating parameters used by the microcontroller 360 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other exemplary pacing parameters include base rate, rest rate and circadian base rate.

Advantageously, the operating parameters of the implantable pacer/ICD 10 may be non-invasively programmed into the memory 218 through a telemetry circuit 400 in telemetric communication with the external device 12, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 218) to be sent to the external device 12 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may, depending upon its capabilities, further be used to detect changes in cardiac output, changes in the physiological condition of the heart, or diurnal changes in activity (e.g., detecting sleep and wake states) and to detect arousal from sleep.

Accordingly, the microcontroller 360 responds by adjusting the various pacing parameters (such as rate, AV Delay, V-V Delay, etc.) at which the atrial and ventricular pulse generators, 370 and 372, generate stimulation pulses. While shown as being included within pacer/ICD 10, it is to be understood that the sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 20. The battery 410 may vary depending on the capabilities of pacer/ICD 10. If the system only provides low voltage therapy, a lithium iodine or lithium copper fluoride cell may be utilized. For pacer/ICD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, pacer/ICD 10 is preferably capable of high voltage therapy and batteries or other power sources appropriate for that purpose are employed.

As further shown in FIG. 20, pacer/ICD 10 is shown as having an impedance measuring circuit 412 which is enabled by the microcontroller 360 via a control signal 414. Uses for an impedance measuring circuit include, but are not limited to, lead impedance surveillance for detecting breaks in the lead; measuring respiration or minute ventilation; measuring thoracic impedance for determining shock thresholds; detecting when the device has been implanted; measuring stroke volume; and detecting the opening of heart valves, etc. The impedance measuring circuit 412 is advantageously coupled to the switch 374 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes one of which may be the device can with the other electrode typically selected from the left atrial coil electrode 328, the RV coil electrode 336, and/or the SVC coil electrode 338. Cardioversion shocks are generally considered to be of low to moderate energy level (so as to save battery power and to minimize pain felt by the patient to the extent possible), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and typically pertain to the treatment of fibrillation. Accordingly, the microcontroller 360 is capable of controlling the synchronous or asynchronous delivery of the shocking pulses.

Microcontroller 360 also includes: a noise detector 401 operative to detect an amount of electrical noise within a channel in which electrical cardiac signals are sensed; an electrical cardiac event detector 403 operative to detect parameters representative of depolarization and repolarization events within the electrical cardiac signals; and an ASC parameter adjustment unit 405 operative to set the programmable sensitivity adjustment parameters (i.e. the ASC parameters) based on the parameters representative of depolarization and repolarization events and, in some examples, further based on the amount of electrical noise (generally in accordance with techniques describe above in connection with FIGS. 3-6 and FIGS. 8-18.) The microcontroller also includes a profile determination unit 407 operative to determine a profile representative of the shape of the cardiac signal and a profile-based programmable parameter adjustment unit 409 operative to set the programmable sensitivity adjustment parameters based on the profile representative of the shape of the cardiac signals (generally in accordance with techniques described above in connection with FIGS. 3 and 7.) Depending upon the implementation, the various components of the microcontroller may be implemented as separate software or hardware modules. However, the modules may be combined to permit single modules to perform multiple functions.

In general, the various functional components of the exemplary systems described herein may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention. Note also that the term "including" as used herein is intended to be inclusive, i.e. "including but not limited to."

What is claimed is:

1. A method for use by an implantable medical device capable of automatically adjusting a sensitivity with which electrical cardiac signals are sensed within a patient, the method comprising:

sensing electrical cardiac signals within the patient while adjusting the sensitivity during individual cardiac cycles in accordance with a sensitivity adjustment procedure specified by a plurality of sensitivity adjustment parameters including, at least, a Decay Rate and one or more of a Starting Sensitivity parameter specifying a Starting Sensitivity for use following detection of a sensed event, a Decay Delay parameter specifying a duration of time during an individual cardiac cycle following the sensed event before sensitivity is automatically decreased, a Refractory Interval specifying a duration of time during an individual cardiac cycle following a sensed event during which any further events are not sensed, wherein the Decay Rate specifies a rate by which the sensitivity is changed during an individual cardiac cycle following completion of the Decay Delay;

detecting depolarization and repolarization event parameters within the electrical cardiac signals, including depolarization event amplitudes, depolarization event widths and repolarization event amplitudes;

determining a set of comparisons by comparing each of the detected parameters to a corresponding nominal value of the parameter to determine if the detected parameter is at its nominal value, larger than its nominal value or smaller than its nominal value; and resetting the sensitivity adjustment parameters, including selectively resetting the Decay Rate and one or more of the Starting Sensitivity, the Decay Delay and the Refractory Interval, based on the set of comparisons wherein, if the depolarization amplitude is larger than its nominal value, the depolarization width is at its nominal value and the repolarization amplitude is smaller than its nominal value, then the adjustment parameters are maintained at nominal values.

2. A method for use by an implantable medical device capable of automatically adjusting a sensitivity with which electrical cardiac signals are sensed within a patient, the method comprising:

sensing electrical cardiac signals within the patient while adjusting the sensitivity during individual cardiac cycles in accordance with a sensitivity adjustment procedure specified by a plurality of sensitivity adjustment parameters including, at least, a Decay Rate and one or more of a Starting Sensitivity parameter specifying a Starting Sensitivity for use following detection of a sensed event, a Decay Delay parameter specifying a duration of time during an individual cardiac cycle following the sensed event before sensitivity is automatically decreased, a Refractory Interval specifying a duration of time during an individual cardiac cycle following a sensed event during which any further events are not sensed, wherein the Decay Rate specifies a rate by which the sensitivity is changed during an individual cardiac cycle following completion of the Decay Delay;

detecting depolarization and repolarization event parameters within the electrical cardiac signals, including depolarization event amplitudes, depolarization event widths and repolarization event amplitudes;

determining a set of comparisons by comparing each of the detected parameters to a corresponding nominal value of the parameter to determine if the detected parameter is at its nominal value, larger than its nominal value or smaller than its nominal value; and resetting the sensitivity adjustment parameters, including selectively resetting the Decay Rate and one or more of the Starting Sensitivity, the Decay Delay and the Refractory Interval, based on the set of comparisons wherein, if the depolarization amplitude is larger than its nominal value, the depolarization width is at its nominal value and the repolarization amplitude is larger than its nominal value, then a Decay Delay value is reset to be longer than a nominal value of Decay Delay, the Decay Rate value is reset to be slower than a nominal value of Decay Rate, and a Refractory Interval (VREF) value is reset to be longer than a nominal value of VREF.

3. A method for use by an implantable medical device capable of automatically adjusting a sensitivity with which electrical cardiac signals are sensed within a patient, the method comprising:

sensing electrical cardiac signals within the patient while adjusting the sensitivity during individual cardiac cycles in accordance with a sensitivity adjustment procedure specified by a plurality of sensitivity adjustment parameters including, at least, a Decay Rate and one or more of a Starting Sensitivity parameter specifying a Starting Sensitivity for use following detection of a sensed event, a Decay Delay parameter specifying a duration of time during an individual cardiac cycle following the sensed event before sensitivity is automatically decreased, a Refractory Interval specifying a duration of time during an individual cardiac cycle following a sensed event during which any further events are not sensed, wherein the Decay Rate specifies a rate by which the sensitivity is changed during an individual cardiac cycle following completion of the Decay Delay;

detecting depolarization and repolarization event parameters within the electrical cardiac signals, including depolarization event amplitudes, depolarization event widths and repolarization event amplitudes;

determining a set of comparisons by comparing each of the detected parameters to a corresponding nominal value of the parameter to determine if the detected parameter is at its nominal value, larger than its nominal value or smaller than its nominal value; and resetting the sensitivity adjustment parameters, including selectively resetting the Decay Rate and one or more of the Starting Sensitivity, the Decay Delay and the Refractory Interval, based on the set of comparisons wherein, if the depolarization amplitude is at its nominal value, the depolarization width at its nominal value and the repolarization amplitude is smaller than its nominal value, then a Decay Delay value of is reset to zero and Starting Sensitivity value is reset to be lower than a nominal value of Starting Sensitivity.

4. A method for use by an implantable medical device capable of automatically adjusting a sensitivity with which electrical cardiac signals are sensed within a patient, the method comprising:

sensing electrical cardiac signals within the patient while adjusting the sensitivity during individual cardiac cycles in accordance with a sensitivity adjustment procedure specified by a plurality of sensitivity adjustment parameters including, at least, a Decay Rate, and one or more of a Starting Sensitivity parameter specifying a Starting Sensitivity for use following detection of a sensed event, a Decay Delay parameter specifying a duration of time during an individual cardiac cycle following the sensed event before sensitivity is automatically decreased, a Refractory Interval specifying a duration of time during an individual cardiac cycle following a sensed event during which any further events are not sensed, wherein the Decay Rate specifies a rate by which the sensitivity is changed during an individual cardiac cycle following completion of the Decay Delay;

detecting depolarization and repolarization event parameters within the electrical cardiac signals, including depolarization event amplitudes, depolarization event widths and repolarization event amplitudes;

determining a set of comparisons by comparing each of the detected parameters to a corresponding nominal value of the parameter to determine if the detected parameter is at its nominal value, larger than its nominal value or smaller than its nominal value; and resetting the sensitivity adjustment parameters, including selectively resetting the Decay Rate and one or more of the Starting Sensitivity, the Decay Delay and the Refractory Interval, based on the set of comparisons wherein, if the depolarization amplitude is larger than its nominal value, the depolarization width is at its nominal value and the repolarization amplitude is smaller than its nominal value, then a Decay Delay value is reset to zero and a Refractory Interval (VREF) value is reset to be equal to the width of the depolarization events plus a safety margin.

5. A method for use by an implantable medical device capable of automatically adjusting a sensitivity with which electrical cardiac signals are sensed within a patient, the method comprising:

sensing electrical cardiac signals within the patient while adjusting the sensitivity during individual cardiac cycles in accordance with a sensitivity adjustment procedure specified by a plurality of sensitivity adjustment parameters including, at least, a Decay Rate and one or more of a Starting Sensitivity parameter specifying a Starting Sensitivity for use following detection of a sensed event, a Decay Delay parameter specifying a duration of time during an individual cardiac cycle following the sensed event before sensitivity is automatically decreased, a Refractory Interval specifying a duration of time during an individual cardiac cycle following a sensed event during which any further events are not sensed, wherein the Decay Rate specifies a rate by which the sensitivity is changed during an individual cardiac cycle following completion of the Decay Delay;

detecting depolarization and repolarization event parameters within the electrical cardiac signals, including depolarization event amplitudes, depolarization event widths and repolarization event amplitudes;

determining a set of comparisons by comparing each of the detected parameters to a corresponding nominal value of the parameter to determine if the detected parameter is at its nominal value, larger than its nominal value or smaller than its nominal value; and resetting the sensitivity adjustment parameters, including selectively resetting the Decay Rate and one or more of the Starting Sensitivity, the Decay Delay and the Refractory Interval, based on the set of comparisons wherein, if the depolarization amplitude is at its nominal value, the depolarization width is larger than its nominal value and the repolarization amplitude is smaller than its nominal value, then a Decay Delay value is reset to zero, a Starting Sensitivity is reset to be lower than a nominal Starting Sensitivity and a Refractory Interval (VREF) value is reset to be equal to the width of the depolarization events plus a safety margin.

6. A method for use by an implantable medical device capable of automatically adjusting a sensitivity with which electrical cardiac signals are sensed within a patient, the method comprising:

sensing electrical cardiac signals within the patient while adjusting the sensitivity during individual cardiac cycles in accordance with a sensitivity adjustment procedure specified by a plurality of sensitivity adjustment parameters including, at least, a Decay Rate and one or more of a Starting Sensitivity parameter specifying a Starting Sensitivity for use following detection of a sensed event, a Decay Delay parameter specifying a duration of time during an individual cardiac cycle following the sensed event before sensitivity is automatically decreased, a Refractory Interval specifying a duration of time during an individual cardiac cycle following a sensed event during which any further events are not sensed, wherein the Decay Rate specifies a rate by which the sensitivity is changed during an individual cardiac cycle following completion of the Decay Delay;

detecting depolarization and repolarization event parameters within the electrical cardiac signals, including depolarization event amplitudes, depolarization event widths and repolarization event amplitudes;

determining a set of comparisons by comparing each of the detected parameters to a corresponding nominal value of the parameter to determine if the detected parameter is at its nominal value, larger than its nominal value or smaller than its nominal value; and resetting the sensitivity adjustment parameters, including selectively resetting the Decay Rate and one or more of the Starting Sensitivity, the Decay Delay and the Refractory Interval, based on the set of comparisons wherein, if the depolarization amplitude is at its nominal value, the depolarization width is larger than its nominal value and the repolarization amplitude is at its nominal value, then a Decay Delay value is reset to an RT interval plus a safety margin, and a Starting Sensitivity is reset to be lower than a nominal Starting Sensitivity.

7. A method for use by an implantable medical device capable of automatically adjusting a sensitivity with which electrical cardiac signals are sensed within a patient, the method comprising:

sensing electrical cardiac signals within the patient while adjusting the sensitivity during individual cardiac cycles in accordance with a sensitivity adjustment procedure specified by a plurality of sensitivity adjustment parameters including, at least, a Decay Rate and one or more of a Starting Sensitivity parameter specifying a Starting Sensitivity for use following detection of a sensed event, a Decay Delay parameter specifying a duration of time during an individual cardiac cycle following the sensed event before sensitivity is automatically decreased, a Refractory Interval specifying a duration of time during an individual cardiac cycle following a sensed event during which any further events are not sensed, wherein the Decay Rate specifies a rate by which the sensitivity is changed during an individual cardiac cycle following completion of the Decay Delay;

detecting depolarization and repolarization event parameters within the electrical cardiac signals, including depolarization event amplitudes, depolarization event widths and repolarization event amplitudes;

determining a set of comparisons by comparing each of the detected parameters to a corresponding nominal value of the parameter to determine if the detected parameter is at its nominal value, larger than its nominal value or smaller than its nominal value; and resetting the sensitivity adjustment parameters, including selectively resetting the Decay Rate and one or more of the Starting Sensitivity, the Decay Delay and the Refractory Interval, based on the set of comparisons wherein, if the depolarization amplitude is at its nominal value, the depolarization width is at its nominal value and the repolarization amplitude is at its nominal value, then a Decay Delay value of the adjustment procedure is reset to an RT interval plus a safety margin, and a Starting Sensitivity is reset to be substantially higher than a nominal Starting Sensitivity.

8. A method for use by an implantable medical device capable of automatically adjusting a sensitivity with which electrical cardiac signals are sensed within a patient, the method comprising:

sensing electrical cardiac signals within the patient while adjusting the sensitivity during individual cardiac cycles in accordance with a sensitivity adjustment procedure specified by a plurality of sensitivity adjustment parameters including, at least, a Decay Rate and one or more of a Starting Sensitivity parameter specifying a Starting Sensitivity for use following detection of a sensed event, a Decay Delay parameter specifying a duration of time during an individual cardiac cycle following the sensed event before sensitivity is automatically decreased, a Refractory Interval specifying a duration of time during an individual cardiac cycle following a sensed event during which any further events are not sensed, wherein the Decay Rate specifies a rate by which the sensitivity is changed during an individual cardiac cycle following completion of the Decay Delay;

detecting depolarization and repolarization event parameters within the electrical cardiac signals, including depolarization event amplitudes, depolarization event widths and repolarization event amplitudes;

determining a set of comparisons by comparing each of the detected parameters to a corresponding nominal value of the parameter to determine if the detected parameter is at its nominal value, larger than its nominal value or smaller than its nominal value; and resetting the sensitivity adjustment parameters, including selectively resetting the Decay Rate and one or more of the Starting Sensitivity, the Decay Delay and the Refractory Interval, based on the set of comparisons wherein, if the depolarization amplitude is at its nominal value, the depolarization width is smaller than its nominal value and the repolarization amplitude is larger than its nominal value, then a Decay Delay value is reset to an RT interval plus a safety margin, and a Starting Sensitivity is reset to be higher than a nominal Starting Sensitivity and a Refractory Interval (VREF) value is reset to a floating value.

* * * * *